(12) United States Patent
Burdette et al.

(10) Patent No.: US 7,438,685 B2
(45) Date of Patent: Oct. 21, 2008

(54) APPARATUS AND METHOD FOR REGISTRATION, GUIDANCE AND TARGETING OF EXTERNAL BEAM RADIATION THERAPY

(75) Inventors: Everette C. Burdette, Champaign, IL (US); Dana L. Deardorff, Oakland, CA (US)

(73) Assignee: Computerized Medical Systems, Inc., St. Louis, MO (US)

( * ) Notice: Subject to any disclaimer, the term of this patent is extended or adjusted under 35 U.S.C. 154(b) by 1019 days.

(21) Appl. No.: 10/286,368

(22) Filed: Nov. 1, 2002

(65) Prior Publication Data

US 2003/0112922 A1    Jun. 19, 2003

Related U.S. Application Data

(60) Provisional application No. 60/337,449, filed on Nov. 5, 2001.

(51) Int. Cl.
*A61B 8/00*    (2006.01)

(52) U.S. Cl. ....................................... 600/439

(58) Field of Classification Search .................. 600/437, 600/439, 443, 447, 462–463, 471, 1–3, 6–8; 128/916; 378/65, 68–69
See application file for complete search history.

(56) References Cited

U.S. PATENT DOCUMENTS

| 4,125,858 A | 11/1978 | Hounsfield et al. |
| 4,567,896 A | 2/1986 | Barnea et al. |
| 4,586,512 A | 5/1986 | Do-huu et al. |
| 4,751,643 A | 6/1988 | Lorensen et al. |
| 4,764,971 A | 8/1988 | Sullivan |
| 4,791,567 A | 12/1988 | Cline et al. |

(Continued)

FOREIGN PATENT DOCUMENTS

DE    198 25 999    12/1999

(Continued)

OTHER PUBLICATIONS

Patent Cooperation Treaty; International Search Report; Jan. 29, 2003.

(Continued)

*Primary Examiner*—Francis J. Jaworski
(74) *Attorney, Agent, or Firm*—Thompson Coburn LLP; Benjamin L. Volk, Jr.

(57) ABSTRACT

An improved system and method for optimizing the planning, registration, targeting, and delivery of conformal, external beam radiation therapy of prostate cancer and other soft-tissue diseases. Real-time ultrasound imaging during planning and treatment is used for localization of soft tissue treatment targets and fused with radiographic or CT data for conformal treatment optimization. The fusion technique provides accurate localization of the prostate volume in real time. For treatment of prostate cancer, visualization of the prostate gland is achieved using transrectal ultrasonography and the fusion of that image in the precise location of the prostate within the pelvic region, accurately determining the location of the prostate target by transformation of the ultrasound image data on both the ultrasound and X-ray/CT images. The radiation field may be optimized to significantly reduce the volume of irradiated normal tissue, minimizing the exposure of the surrounding healthy tissues and increasing dosage delivered to the prostate treatment target.

59 Claims, 9 Drawing Sheets

U.S. PATENT DOCUMENTS

| | | |
|---|---|---|
| 4,856,074 A | 8/1989 | Nagaoka |
| 4,896,673 A | 1/1990 | Rose et al. |
| 4,961,425 A | 10/1990 | Kennedy et al. |
| 4,991,579 A | 2/1991 | Allen |
| 4,994,013 A | 2/1991 | Suthanthiran et al. |
| 5,072,384 A | 12/1991 | Doi et al. |
| 5,133,020 A | 7/1992 | Giger et al. |
| 5,166,876 A | 11/1992 | Cline et al. |
| 5,170,790 A | 12/1992 | Lacoste et al. |
| 5,178,148 A | 1/1993 | Lacoste et al. |
| 5,185,809 A | 2/1993 | Kennedy et al. |
| 5,187,658 A | 2/1993 | Cline et al. |
| 5,204,625 A | 4/1993 | Cline et al. |
| 5,222,499 A | 6/1993 | Allen et al. |
| 5,227,969 A | 7/1993 | Waggener et al. |
| 5,234,004 A | 8/1993 | Hascoet et al. |
| 5,239,591 A | 8/1993 | Ranganath |
| 5,242,373 A | 9/1993 | Scott et al. |
| 5,260,871 A | 11/1993 | Goldberg |
| 5,289,374 A | 2/1994 | Doi et al. |
| 5,299,253 A | 3/1994 | Wessels |
| 5,319,549 A | 6/1994 | Katsuragawa et al. |
| 5,319,551 A | 6/1994 | Sekiguchi et al. |
| 5,339,812 A | 8/1994 | Hardy et al. |
| 5,371,810 A | 12/1994 | Vaidyanathan |
| 5,389,101 A | 2/1995 | Heilbrun et al. |
| 5,391,139 A * | 2/1995 | Edmundson .................. 600/7 |
| 5,391,199 A | 2/1995 | Ben-Haim |
| 5,394,457 A | 2/1995 | Leibinger et al. |
| 5,398,690 A | 3/1995 | Batten et al. |
| 5,409,006 A | 4/1995 | Buchholtz et al. |
| 5,410,617 A | 4/1995 | Kidd et al. |
| 5,411,026 A | 5/1995 | Carol |
| 5,412,563 A | 5/1995 | Cline et al. |
| 5,433,199 A | 7/1995 | Cline et al. |
| 5,447,154 A * | 9/1995 | Cinquin et al. .............. 600/429 |
| 5,452,367 A | 9/1995 | Bick et al. |
| 5,457,754 A | 10/1995 | Han et al. |
| 5,458,126 A | 10/1995 | Cline et al. |
| 5,460,592 A | 10/1995 | Langton et al. |
| 5,491,627 A | 2/1996 | Zhang et al. |
| 5,494,039 A | 2/1996 | Onik et al. |
| 5,517,602 A | 5/1996 | Natarajan |
| 5,526,812 A | 6/1996 | Dumoulin et al. |
| 5,531,223 A | 7/1996 | Hatanaka |
| 5,531,227 A | 7/1996 | Schneider |
| 5,537,485 A | 7/1996 | Nishikawa et al. |
| 5,553,207 A | 9/1996 | Sekiguchi et al. |
| 5,562,095 A | 10/1996 | Downey et al. |
| 5,566,246 A | 10/1996 | Rao |
| 5,570,430 A | 10/1996 | Sheehan et al. |
| 5,574,799 A | 11/1996 | Bankman et al. |
| 5,583,659 A | 12/1996 | Lee et al. |
| 5,588,430 A * | 12/1996 | Bova et al. .................. 600/429 |
| 5,590,215 A | 12/1996 | Allen |
| 5,603,318 A | 2/1997 | Heilbrun et al. |
| 5,622,170 A | 4/1997 | Schulz |
| 5,624,382 A | 4/1997 | Oppelt et al. |
| 5,638,819 A | 6/1997 | Manwaring et al. |
| 5,640,496 A | 6/1997 | Hardy et al. |
| 5,660,185 A | 8/1997 | Shmulewitz et al. |
| 5,662,111 A | 9/1997 | Cosman |
| 5,669,382 A | 9/1997 | Curwen et al. |
| 5,672,172 A | 9/1997 | Zupkas |
| 5,682,886 A | 11/1997 | Delp et al. |
| 5,709,206 A | 1/1998 | Teboul |
| 5,715,836 A | 2/1998 | Kliegis et al. |
| 5,727,538 A | 3/1998 | Ellis |
| 5,734,739 A | 3/1998 | Sheehan et al. |
| 5,740,225 A | 4/1998 | Nabatame |
| 5,742,263 A | 4/1998 | Wang et al. |
| 5,749,362 A | 5/1998 | Funda et al. |
| 5,765,561 A | 6/1998 | Chen et al. |
| 5,769,074 A | 6/1998 | Barnhill et al. |
| 5,776,063 A | 7/1998 | Dittrich et al. |
| 5,778,043 A | 7/1998 | Cosman |
| 5,787,886 A | 8/1998 | Kelly et al. |
| 5,797,849 A | 8/1998 | Vesely et al. |
| 5,810,007 A | 9/1998 | Holupka et al. |
| 5,817,022 A | 10/1998 | Vesely |
| 5,820,623 A | 10/1998 | Ng |
| 5,830,145 A | 11/1998 | Tenhoff |
| 5,833,627 A | 11/1998 | Shmulewitz et al. |
| 5,836,954 A | 11/1998 | Heilbrun et al. |
| 5,851,183 A | 12/1998 | Bucholz |
| 5,859,891 A | 1/1999 | Hibbard |
| 5,860,909 A | 1/1999 | Mick et al. |
| 5,868,673 A | 2/1999 | Vesely |
| 5,868,757 A | 2/1999 | Koutrouvelis |
| 5,871,448 A | 2/1999 | Ellard |
| 5,891,034 A | 4/1999 | Bucholz |
| 5,906,574 A | 5/1999 | Kan |
| 5,928,130 A | 7/1999 | Schmidt |
| 5,931,786 A | 8/1999 | Whitmore, III et al. |
| 5,938,583 A | 8/1999 | Grimm |
| 5,951,571 A | 9/1999 | Audette |
| 5,961,527 A | 10/1999 | Whitmore, III et al. |
| 5,974,165 A | 10/1999 | Giger et al. |
| 5,984,870 A | 11/1999 | Giger et al. |
| 5,989,811 A | 11/1999 | Veltri et al. |
| 6,004,267 A | 12/1999 | Tewari et al. |
| 6,006,126 A | 12/1999 | Cosman |
| 6,007,474 A | 12/1999 | Rydell |
| 6,025,128 A | 2/2000 | Veltri et al. |
| 6,027,446 A | 2/2000 | Pathak et al. |
| 6,033,357 A | 3/2000 | Ciezki et al. |
| 6,036,632 A | 3/2000 | Whitmore, III et al. |
| 6,038,467 A | 3/2000 | De Blick et al. |
| 6,048,312 A | 4/2000 | Ishrak et al. |
| 6,083,166 A | 7/2000 | Holdaway et al. |
| 6,083,167 A | 7/2000 | Fox et al. |
| 6,095,975 A | 8/2000 | Silvern |
| 6,102,844 A | 8/2000 | Ravins et al. |
| 6,102,867 A | 8/2000 | Dietz et al. |
| 6,129,670 A | 10/2000 | Burdette et al. |
| 6,140,065 A | 10/2000 | Carlson et al. |
| 6,144,875 A * | 11/2000 | Schweikard et al. ........ 600/427 |
| 6,146,390 A | 11/2000 | Heilbrun et al. |
| 6,165,181 A | 12/2000 | Heilbrun et al. |
| 6,167,296 A | 12/2000 | Shahidi |
| 6,179,768 B1 | 1/2001 | Loffler et al. |
| 6,196,963 B1 | 3/2001 | Williams |
| 6,196,964 B1 | 3/2001 | Loffler et al. |
| 6,206,832 B1 | 3/2001 | Downey et al. |
| 6,208,883 B1 * | 3/2001 | Holupka et al. ............. 600/407 |
| 6,210,315 B1 | 4/2001 | Andrews et al. |
| 6,213,110 B1 | 4/2001 | Christopher et al. |
| 6,213,932 B1 | 4/2001 | Schmidt |
| 6,219,403 B1 * | 4/2001 | Nishihara .................... 378/65 |
| 6,226,543 B1 | 5/2001 | Gilboa et al. |
| 6,236,875 B1 | 5/2001 | Bucholz et al. |
| 6,238,342 B1 | 5/2001 | Feleppa et al. |
| 6,241,670 B1 | 6/2001 | Nambu |
| 6,249,594 B1 | 6/2001 | Hibbard |
| 6,256,529 B1 | 7/2001 | Holupka et al. |
| 6,261,219 B1 | 7/2001 | Meloul et al. |
| 6,266,453 B1 | 7/2001 | Hibbard et al. |
| 6,270,472 B1 | 8/2001 | Antaki et al. |
| 6,301,495 B1 | 10/2001 | Gueziec et al. |
| 6,311,084 B1 | 10/2001 | Cormack et al. |
| 6,325,758 B1 * | 12/2001 | Carol et al. ................. 600/439 |
| 6,332,888 B1 | 12/2001 | Levy et al. |
| 6,354,989 B1 | 3/2002 | Nudeshima |
| 6,358,195 B1 | 3/2002 | Green et al. |

| | | |
|---|---|---|
| 6,361,487 B1 | 3/2002 | Green et al. |
| 6,366,796 B1 | 4/2002 | Yanof et al. |
| 6,379,302 B1 | 4/2002 | Kessman et al. |
| 6,387,034 B1 | 5/2002 | Lee |
| 6,387,035 B1 | 5/2002 | Jung, Jr. et al. |
| 6,416,492 B1 | 7/2002 | Nielson |
| 6,423,009 B1 | 7/2002 | Downey et al. |
| 6,425,865 B1 | 7/2002 | Salcudean et al. |
| 6,454,696 B1 | 9/2002 | Kindlein et al. |
| 6,490,475 B1 | 12/2002 | Seeley et al. |
| 6,500,109 B2 | 12/2002 | Tokita et al. |
| 6,512,942 B1 | 1/2003 | Burdette et al. |
| 6,572,525 B1 | 6/2003 | Yoshizumi |
| 6,612,991 B2 | 9/2003 | Sauer et al. |
| 6,662,036 B2 * | 12/2003 | Cosman ................. 600/411 |
| 6,766,036 B1 | 7/2004 | Pryor |
| 6,775,404 B1 | 8/2004 | Pagoulatos et al. |
| 6,796,943 B2 * | 9/2004 | Mochizuki ............ 600/437 |
| 2001/0029334 A1 | 10/2001 | Graumann et al. |
| 2002/0077546 A1 | 6/2002 | Aldefeld et al. |
| 2002/0087080 A1 | 7/2002 | Slayton et al. |
| 2003/0074011 A1 | 4/2003 | Gilboa et al. |

FOREIGN PATENT DOCUMENTS

| | | |
|---|---|---|
| EP | 0 424 912 | 5/1991 |
| EP | 0 455 439 A2 | 11/1991 |
| WO | WO 91/07726 | 5/1991 |
| WO | WO 96/10949 | 4/1996 |
| WO | WO 96/11624 | 4/1996 |
| WO | WO 96/42070 | 12/1996 |
| WO | WO 98/39736 | 9/1998 |
| WO | WO 99/27839 | 6/1999 |
| WO | WO 00/14668 | 3/2000 |
| WO | WO 00/63658 | 10/2000 |
| WO | WO 01/06924 | 2/2001 |
| WO | WO 01/87164 | 11/2001 |
| WO | WO 01/95795 | 12/2001 |
| WO | WO 02/44749 | 6/2002 |

OTHER PUBLICATIONS

Adams and Bischof; "Seeded Region Growing"; *IEEE Transactions on Pattern Analysis and Machine Intelligence*; Jun. 1994; pp. 641-647; vol. 16, No. 6.

Anuta, P.E., Oct. 1970 IEEE Transactions on Geoscience Electronics, vol. GE-8, No. 4, "Spatial Registration of Multispectrical and Multitemporal Digital Imagery Using Fast Fourier Transform Techniques", pp. 353-368.

Ballard and Brown; *Computer Vision*; 1982; pp. 119-165; Chapters 4-5; Prentice-Hall, Inc., Englewood Cliffs, New Jersey.

Barnea and Silverman, Feb. 1972 IEEE Transactions on Computers, vol. C-21, No. 2, "A Class of Algorithms for Fast Digital Image Registration", pp. 179-186.

Besag; "On the Statistical Analysis of Dirty Pictures"; *Journal of the Royal Statistical Society*; 1986; pp. 259-279; vol. 48, No. 3.

Beveridge, Griffith, Kohler, Hanson and Riseman; "Segmenting Images Using Localized Histograms and Region Merging"; *International Journal of Computer Vision*; 1989; pp. 311-347; vol. 2; Kluwer Academic Publishers, Boston.

Bezdek et al.; "Review of MR image segmentation techniques using pattern recognition"; Medical Physics; vol. 20(4); pp. 1033-1048; 1993.

Brown, L.G., Dec. 1992 ACM Computing Surveys vol. 24 No. 4, "A Survey of Image Registration Techniques", pp. 325-378.

Chakraborty et al.; Deformable boundary finding in medical images by integrating gradient and region information; IEEE Transactions on Medical Imaging; vol. 15; pp. 859-870; 1996.

Cline et al. "3D reconstruction of the brain from magnetic resonance images using a connectivity algorithm"; Magnetic Resonance Imaging; vol. 5; pp. 345-352; 1987.

Cline et al.; "Three-dimensional segmentation of MR images of the head using probability and connectivity"; Journal of Computer Assisted Tomography; vol. 14(6); pp. 1037-1045; 1990.

Cline et al.; "Vascular morphology by three-dimensional magnetic resonance imaging"; Magnetic Resonance Imaging; vol. 7; pp. 45-54; 1989.

Cohen; "On Active Contour Models and Balloons"; *CVGIP: Image Understanding*; Mar. 1991; pp. 211-218; vol. 53, No. 2; Academic Press, Inc.

Collignon, A., et al., Apr. 1995 Proc. of the Xvth Int'l. Conf. On Computer Vision, Virtual Reality, and Robotics in Medicine (CVRMed '95), vol. 905, "Automated Multi-Modality Image Registration Based On Information Theory", pp. 263-274.

Cover and Thomas; *Elements of Information Theory*; 1991; pp. 12-42, 279-332; Chapters 2, 12; John Wiley & Sons, Inc., New York.

Decarli et al.; "Method for quantification of brain, ventricular, and subarachnoid CSF volumes from MR images"; Journal of Computer Assisted Tomography; vol. 16(2); pp. 274-284; 1992.

Delagnes et al.; "Active contours approach to object tracing in image sequences with complex background"; Pattern Recognition Letters; vol. 16(2); pp. 171-178; 1995.

Devroye, Györfi and Lugosi; *A Probabilistic Theory of Pattern Recognition*; 1996; pp. 9-20, 61-90; Chapters 2, 5; Springer-Verlag New York, Inc.

Diallo, B.; "Conception, realisation et exploitation d'une base de donnees en neuroimagerie cognitive"; Universite de Caen/Basse-Normandi; Mar. 1992; pp. 148-180; Caen, France.

Duda, Hart and Stork; *Pattern Classification*; 2001; pp. 20-83, 161-214; Second Edition, Chapters 2, 4; John Wiley & Sons, Inc., New York.

Duda, Hart and Stork; *Pattern Classification*; 2001; pp. 517-599; Second Edition, Chapter 10; John Wiley & Sons, Inc., New York.

Fletcher et al.; A multispectral analysis of brain tissues; Magnetic Resonance in Medicine; vol. 29; pp. 623-630; 1993.

Fukunaga; *Introduction to Statistical Pattern Recognition*; 1990; pp. 51-123; Second Edition, Chapter 3; Academic Press, Inc., San Diego, California.

Geman and Geman; "Stochastic Relaxation, Gibbs Distributions, and the Bayesian Restoration of Images"; *IEEE Transactions on Pattern Analysis and Machine Intelligence*; Nov. 1984, pp. 721-741; vol. PAMI-6, No. 6.

Giardina and Kuhl; "Accuracy of Curve Approximation by Harmonically Related Vectors with Elliptical Loci"; *Computer Graphics and Image Processing*; 1977; pp. 277-285; vol. 6; Academic Press, Inc.

Gomez-Lopera J F et al.: "An analysis of edge detection by using the Jensen-Shannon divergence" Journal of Mathematical Imaging and Vision, vol. 13, No. 1, Aug. 2000, pp. 35-56, XP008033153 Kluwer Academic Publishers, Netherlands ISSN: 0924-9907 the whole document.

Grimmett and Stirzaker; *Probability and Random Processes*; 1992; pp. 1-21; Second Edition, Chapter 1; Oxford University Press, Oxford.

Haralick and Shapiro; "Image Segmentation Techniques"; *Computer Vision, Graphics, and Image Processing*; 1985; pp. 100-132; vol. 29.

He, Hamza and Krim; "An Information Divergence Measure for ISAR Image Registration"; IEEE Workshop on Statistical Signal Processing; Aug. 2001; Singapore.

Hibbard; "Maximum *a posteriori* Segmentation for Medical Visualization"; IEEE Workshop on Biomedical Image Analysis (WBIA98), Santa Barbara, California; Jun. 1998; pp. 93-102.

Hibbard, et al., Jun. 26, 1987 Science vol. 236, "Three-Dimensional Representation and Analysis of Brain Energy Metabolism", pp. 1641-1646.

Höhne et al.: "Interactive 3D segmentation of MRI and CT volumes using morphological operations"; Journal of Computer Assisted Tomography; vol. 16(2); pp. 285-294; 1992.

Holupka et al.; "Ultrasound image fusions for external beam radiotherapy for prostate cancer"; Int. J. Radiation Oncology Biol. Phys.; vol. 35, No. 5; pp. 975-984; 1996; Elsevier Science Inc., USA.

Kass, Witkin and Terzopoulos; "Snakes: Active Contour Models"; *International Journal of Computer Vision*; 1988; pp. 321-331; vol. 1, No. 4; Kluwer Academic Publishers, Boston.

Kohn et al.; "Analysis of brain and cerebrospinal fluid volumes with MR imaging"; Radiology; vol. 178; pp. 115-122; 1991.

Kuhl and Giardina; "Elliptic Fourier Features of a Closed Contour"; *Computer Graphics and Image Processing*; 1982; pp. 236-258; vol. 18; Academic Press, Inc.

Kullback and Leibler; "On Information and Sufficiency"; *Annals of Mathematical Statistics*; 1951; pp. 79-86; vol. 22.

Kullback; *Information Theory and Statistics*; 1959; pp. 1-35; Chapters 1, 2; Dover Publications, Inc., Mineola, New York.

Lin; "Divergence Measures Based on the Shannon Entropy"; *IEEE Transactions on Information Theory*; Jan. 1991; pp. 145-151; vol. 37, No. 1.

Maes, F., et al., Jun. 1996 IEEE Proceedings of MMBIA, "Multi-Modality Image Registration by Maximization of Mutual Information", pp. 14-22.

Malladi, Sethian and Vemuri; "Shape Modeling with Front Propagation: A Level Set Approach"; *IEEE Transactions on Pattern Analysis and Machine Intelligence*; Feb. 1995; pp. 158-175; vol. 17, No. 2.

McInerney et al.; Deformable models in medical image analysis; Proceedings of Mathematical Methods Biomedical Image Analysis; pp. 171-180; 1996.

Miller et al.; Mathematical textbook of deformable neuroanatomies; Proceedings of the National Academy of Sciences USA; vol. 90; pp. 11944-11948; 1993.

Neal et al.; "Technical Note: Evaluation of a region growing algorithm for segmenting pelvic computed tomography images during radiotherapy planning"; The British Journal of Radiology; vol. 67; pp. 392-395; 1994.

Nocedal and Wright; *Numerical Optimization*; 1999; pp. 10-63; Chapters 2, 3; Springer-Verlag New York, Inc.

Pal and Pal; "A Review on Image Segmentation Techniques"; *Pattern Recognition*; 1993; pp. 1277-1294; vol. 26, No. 9; Great Britain.

Pelizzari, C.A., et al., Jan./Feb. 1989 Journal of Computer Assisted Tomography, vol. 13, No. 1, "Accurate Three-Dimensional Registration of CT, PET, and/or MR Images of the Brain", pp. 20-26.

Pietrzuk, U. et al.; "An Interactive technique for three-dimensional image registration: validation for PET, SPECT, MRI and CT brain studies"; The Journal of Nuclear Medicine; vol. 35, No. 12; Dec. 1994; pp. 2011-2018.

Pietrzuk, U. et al.; "Three-dimensional alignment of functional and morphological tomograms"; Journal of Computer Assisted Tomography; Jan.-Feb. 1990; vol. 14, No. 1; pp. 51-59; USA.

Pratt, W.K., May 1974 IEEE Transactions on Aerospace and Electronic Systems, vol. AES-10, No. 3, "Correlation Techniques of Image Registration", pp. 353-358.

Press, Teukolsky, Vetterling and Flannery; *Numerical Recipes in C++, The Art of Scientific Computing*; 2002; pp. 398-429; Second Edition; Chapter 10; Cambridge University Press, Cambridge, UK.

Principe; Xu and Fisher; "Information—Theoretic Learning" in *Unsupervised Adaptive Filtering*; 1999; pp. 265-319; Wiley, New York.

Rényi; "On Measures of Entropy and Information"; *Proceedings of the Fourth Berkley Symposium on Mathematical Statistics and Probability*; Berkeley, California, Jun.-Jul. 1960; Published 1961; pp. 547-561; vol. I; University of California Press.

Rényi; "Some Fundamental Questions of Information Theory"; *Selected Papers of Alfred Rényi*; 1976; pp. 526-552; vol. 2; Akademia Kiado, Budapest.

Rosenman, J.G., et al., 1998 Int. J. Radiation Oncology Biol. Phys., vol. 40, No. 1, "Image Registration: An Essential Part of Radiation Therapy Treatment Planning", pp. 197-205.

Rosenfeld and Kak; Digital Picture Processing; 1982; pp. 55-190; Second Edition, vol. 2, Chapter 10; Academic Press, New York.

Shannon; "A Mathematical Theory of Communication"; *The Bell System Technical Journal*; Jul., Oct. 1948; pp. 379-423, 623-656; vol. 27.

Staib and Duncan; "Boundary Finding with Parametrically Deformable Models"; *IEEE Transactions on Pattern Analysis and Machine Intelligence*; Nov. 1992; pp. 1061-1075; vol. 14, No. 11.

Studholme, C., et al., 1996 Medical Image Analysis, vol. 1, No. 2, "Automated 3-D Registration of MR and CT Images of the Head", pp. 163-175.

Tang and Ma; "General Scheme of Region Competition Based on Scale Space"; *IEEE Transactions on Pattern Analysis and Machine Intelligence*; Dec. 2001; pp. 1366-1378; vol. 23, No. 12.

Toennies, K. D. et al.; "Registration of 3D objects and surfaces"; IEEE Computer Graphics and Applications; vol. 10, No. 3; May 1, 1990; pp. 52-62; New York.

Unal G et al.: "Active polygons for object tracking" proceedings First International Symposium on 30 Data Processing Visualization and Transmission, Padova, Italy, Jun. 19-21, 2002, Jun. 19, 2002, pp. 696-699, XP002290194 2002, Los Alamitos, CA, USA, IEEE Comput. Sox, USA ISBN: 0-7695-1521-5 sections 2,3.

Vaidyanathan et al.; "Comparison of supervised MRI segmentation methods for tumor volume determination during therapy"; Magnetic Resonance Imaging; vol. 13(5); pp. 719-728; 1995.

Van Den Elsen, P.A., et al., Mar. 1993 IEEE Engineering in Medicine and Biology, "Medical Image Matching—A Review with Classification", pp. 26-39.

Van Herk, M., et al., Jul. 1994 Medical Physics, vol. 21, No. 7, "Automatic Three-Dimensional Correlation of CT-CT, CT-MRI, and CT-SPECT Using Chamfer Matching", pp. 1163-1178.

Van Trees; *Detection, Estimation, and Modulation Theory, Part I Detection, Estimation, and Linear Modulation Theory*; 1968; pp. 19-165; Chapter 2; John Wiley & Sons, Inc., New York.

Viola, P., et al. Jun. 1995 Proc of the Vth Int'l Conf. On Computer Vision, "Alignment by Maximization of Mutual Information", pp. 16-23.

Wells et al.; "Adaptive segmentation of MRI data"; IEEE Transactions on Medical Imaging; vol. 15, No. 4; pp. 429-442; 1996.

Witten and Frank; *Data Mining, Practical Machine Learning Tools and Techniques with Java Implementations*; 2000; pp. 157-227; Chapter 6; Morgan Kaufmann Publishers, San Francisco, California.

Yin et al.; "Comparison of bilateral-subtraction and single-image processing techniques in the computerized detection of mammographic masses"; Investigative Radiology; vol. 28(6); pp. 473-481; 1993.

European Patent Office; Supplementary Search Report dated Jun. 13, 2006.

* cited by examiner

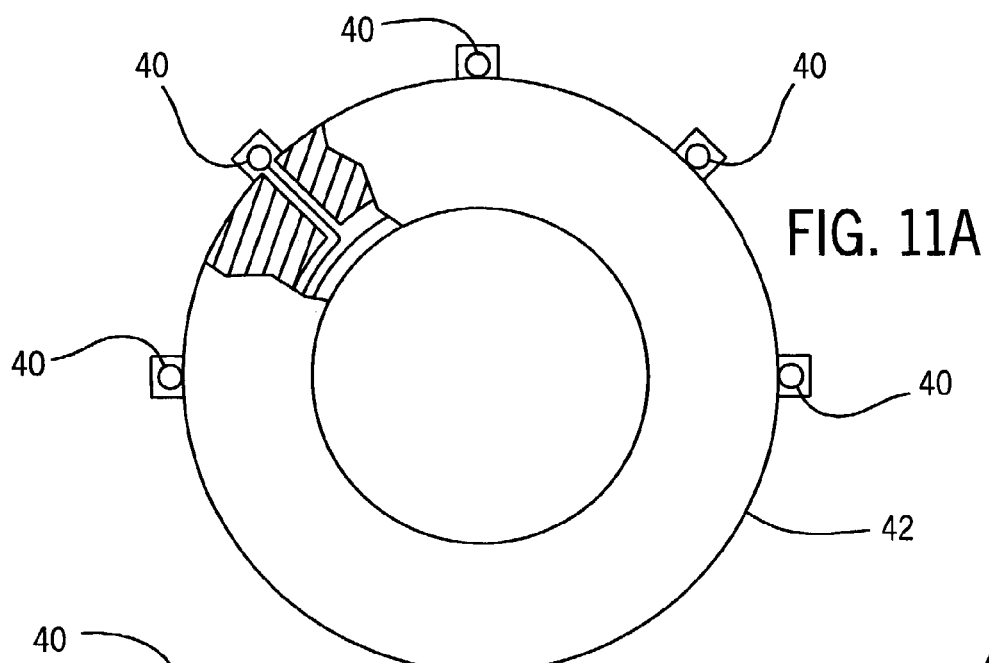
FIG. 11A
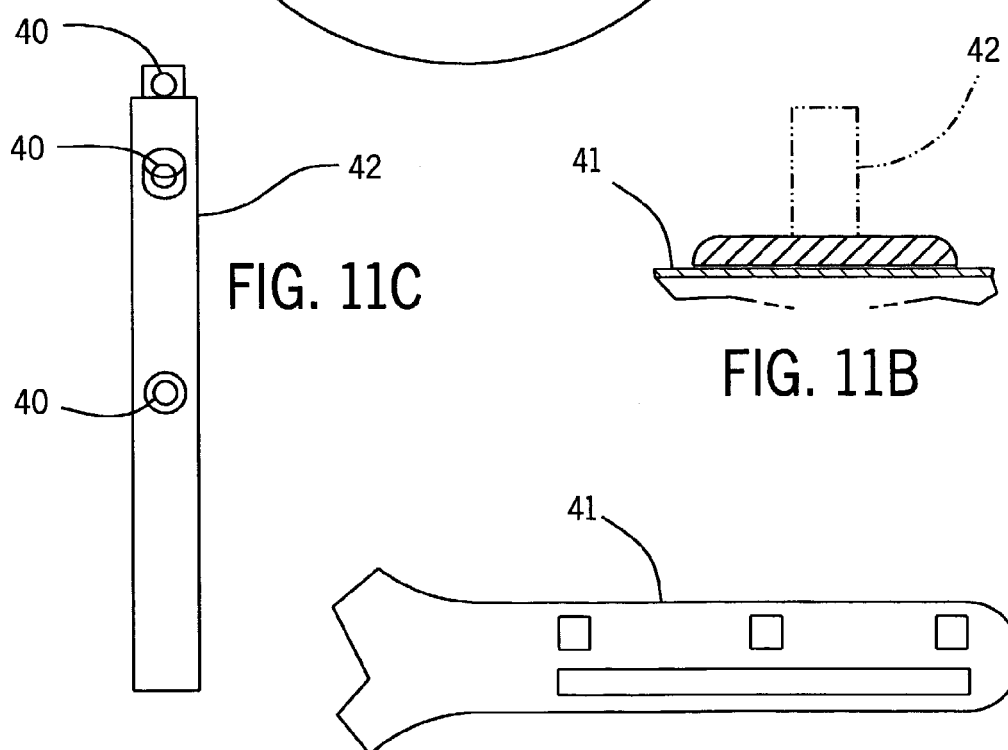
FIG. 11C
FIG. 11B
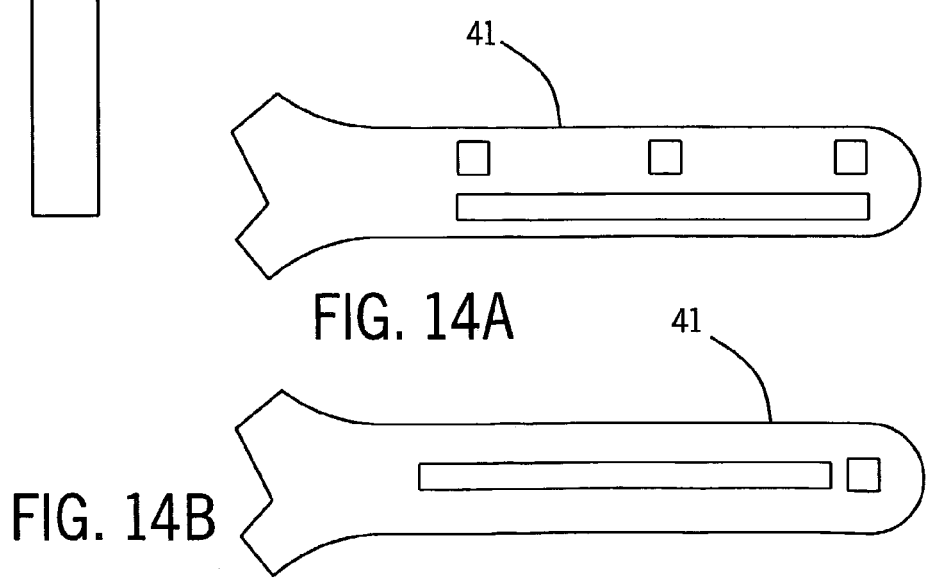
FIG. 14A
FIG. 14B

APPARATUS AND METHOD FOR REGISTRATION, GUIDANCE AND TARGETING OF EXTERNAL BEAM RADIATION THERAPY

FIELD OF THE INVENTION

The present invention relates generally to systems for radiation therapy. More particularly, the present invention relates to a system for targeting soft tissue for external beam radiation therapy.

BACKGROUND OF THE INVENTION

Prostate adenocarcinoma is the most commonly diagnosed cancer in the U.S. male population (excluding skin cancer). Over 20% of these cases are locally-advanced non-metastatic cancers. Treatment for this stage is problematic with significantly low control rates using traditional doses of radiation, which is the main-line therapy. Treatment of prostate cancer is difficult because of the extreme proximal position of tissues that are sensitive to radiation, such as the bladder and rectum. Radiation treatment, which is typically delivered in daily fractionated doses over the course of several weeks, is further complicated by prostate motion relative to the radiation field on a daily basis. More aggressive radiation treatment techniques utilizing conformal fields and higher doses have been used with improved therapeutic results. However, these dose-escalated treatments have met with problems due to increased dose delivered to normal tissues that are in the radiation field, producing many unacceptable complications such as rectal fistulas and bladder perforation and/or sloughing. Therefore, dose-escalated, conformal treatments cannot be delivered without significantly increased morbidity unless the exact position of the prostate can be visualized and registered, and this field localization maintained during the course of the treatment.

The following sections describe in more detail the current treatment model for external beam radiation therapy, including the equipment involved, the procedural methods or phases involved, and the existing problems and limitations.

A linear accelerator ("LINAC") is a treatment device which generates a beam of therapeutic high-energy X rays or electrons. The treatment focus of the beam is the isocenter, which exists at a fixed location with respect to a movable gantry. Moving the gantry allows the angular orientation of the beam (but not the location of the isocenter) to be adjusted. A movable treatment table allows the position and orientation of the isocenter to be adjusted with respect to the patient. The cross-sectional size and shape of the beam can be modified by adjusting the rectangular aperture and by obscuring portions of the resulting rectangular beam, using either custom-cut lead blocks or an automatic multileaf beam collimator. The position of the isocenter for a specific LINAC installation is indicated by orthogonal laser beams. This positional information aids the treatment technician in positioning the patient, treatment table and gantry correctly prior to each treatment. The lasers are aligned with ink marks made on the patient's skin.

An X-ray simulator is a treatment planning device which uses low-energy diagnostic X-rays to simulate an external-beam LINAC treatment. The simulator is a low-energy X-ray unit with a movable gantry and treatment table similar to that of the LINAC. Low-energy beams are directed through the patient at the same angles of incidence which will be used during treatment. The resulting "beams-eye" X-ray images are captured on film and imported into a treatment planning system, where beams are defined, sized, and blocked, and the resulting dose distribution is predicted.

A CT simulator is a treatment planning device which captures transverse CT images referenced to a simulated isocenter. The resulting CT view volume is typically imported directly into a treatment planning system, where beams are defined, sized and blocked, and the resulting dose distribution is predicted. The CT Simulator provides more information than the X-Ray Simulator, because additional anatomical information, including the density of intervening tissue, is visible.

Treatment planning systems include third-party software applications that enable an operator to graphically specify beam apertures conformal to the prostate, based on externally-obtained image data. The radiotherapeutic dose resulting from the specified beams is then computed, and decisions are made with respect to beam energy, number of planned treatments, etc.

The first step in radiation treatment involves simulation, during which an X-ray simulator or CT simulator is used to capture anatomical information about the patient referenced to a simulated treatment isocenter. Using indelible ink, marks are made on the patient's skin indicating the location of the simulated isocenter. Later, these marks will be used to align the patient during treatment. The input to this process is the number of beams to be used and the angles of incidence of each beam, which correspond to the positions of the LINAC gantry to be used at treatment time. Typically, four or six beams are defined. The output of this process is either X-ray images or a CT view volume, spatially referenced to the simulated isocenter.

The second phase involves treatment planning, during which a radiation physicist and radiation oncologist design a multi-beam treatment plan for the patient using a Treatment Planning System (TPS). The input to this process consists of the isocenter-referenced X-ray images or CT view volume resulting from the simulation process, as well as information on the specific LINAC system to be used during treatment. A urologist or radiation oncologist determines the presumed location of the prostate with respect to the isocenter and "contours" or delineates its outline to the TPS. The oncologist defines the apertures and blocking for each beam, thereby defining the cross sectional geometry of each beam. Beams are defined so that the volumetric intersection of the beams conforms as nearly as possible to the presumed location and extent of the prostate. The output of this process is configuration information for the LINAC, including beam apertures, block geometry, beam energy, and beam orientation and also treatment methodology, including the number and frequency of treatments.

The third stage of the LINAC process is the actual treatment delivery, during which a radiologist aligns the patient with respect to the isocenter, using the guidance lasers associated with the LINAC and the ink marks made on the patient's skin during simulation. This is accomplished by moving the patient and/or treatment table as necessary. For each beam defined in the treatment plan, the LINAC is set up with the appropriate gantry angle and beam configuration (field size and blocking), and the specified radiation dosage is delivered.

One of the primary problems associated with radiation treatment of prostate cancer is the location of the prostate during treatment planning. The prostate is not visible on simulation X-rays and is difficult to define in simulation CT data. As a result, during treatment planning, the oncologist must make a judgment determination as to the location of the prostate by reference to nearby structures (e.g. pelvic girdle, bladder, etc.) Variations between patients, especially in prostate size, make this an imperfect process. The resulting beam definitions are not optimally conformal with respect to the prostate, resulting in potential under-dosage of the cancerous tissue and/or overdosage of nearby healthy tissue. The ability to accurately determine the location and extent of the prostate during the treatment planning process would result in better beam/prostate conformance and allow more accurate treatment delivery.

Another significant problem during radiation therapy is caused by prostatic movement between treatment sessions. The patient is positioned at treatment time by aligning the LINAC guiding lasers (indicating the position of the isocenter) with the ink marks on the patient's skin indicating the location of the simulated isocenter. Normal migration of the prostate within the body due to bladder contents, rectal contents, prostatic edema, hormonal therapy, and other factors cannot be accounted for at treatment time. Since numerous treatments are delivered over a period of weeks or months, this migration can result in significant loss of targeting accuracy due to prostatic movement with respect to the isocenter.

Likewise, there is also an issue of prostatic movement during the actual treatment session. After the patient is positioned for treatment, the operator leaves the room and administers the treatment remotely, typically viewing the patient via a closed-circuit video link. Any movement by the patient may move the prostate with respect to the treatment isocenter, reducing beam/prostate conformance and impairing the effectiveness of the treatment.

Another significant issue is the unwanted radiation exposure to the rectum and bladder. Due to the proximity of the rectum to the prostate, treatment plans must be careful to avoid overdosing the rectal wall and the bladder in the course of treating the prostate. The amount of fecal matter in the rectum and the volume of bladder content can affect the dosage received by the posterior wall of the rectum or by the bladder during any given treatment.

One conventional system is marketed as the BAT (B-mode Acquisition Targeting) system by Nomos Corporation. The BAT consists of a transabdominal ultrasound probe attached to a table-mounted localizer arm, and a two-dimensional ultrasound imaging system, which is used to display the prostate during the process of positioning a patient with respect to the isocenter at treatment time. BAT does not offer a treatment planning component.

The BAT system uses a transabdominal TA probe, which can be used by a radiation technician with minimal increase in treatment time, instead of a transrectal (TR) probe. The TR probe provides more reliable imaging of the prostate than the TA probe, since the amount of intervening tissue between the rectum and prostate is small and patient size has little effect on the relevant geometry. Patient size can have a significant effect on the ability of a TA probe to view the prostate.

The BAT provides two-dimensional imaging and must be moved by an operator to offer different spatial views of the prostate. The BAT cannot be used during treatment, because it would interfere with the therapeutic beams and because it would be difficult to ensure continued ultrasound-transparent contact with the patient throughout the treatment. Consequently the BAT is used only during patient set-up. Furthermore, the BAT is not integrated with the treatment plan and is only used to visually position the center of the prostate with respect to the isocenter.

SUMMARY OF THE INVENTION

It is therefore an object of the invention to provide an improved, integrated system with software for ultrasound imaging as part of therapeutic radiation treatment.

It is another object of the invention to provide an improved frameless stereotactic spatial registration system for soft tissue therapy procedures.

It is an additional object of the invention to provide an improved system for the generation of anatomy segmentation for patient treatment protocols.

It is yet another object of the invention to provide an improved imaging system for a patient threatment facility and which includes a therapeutic radiation beam's eye views and is also capable of controlling a field size.

It is still another object of the invention to provide an improved imaging system that is seamlessly integrated with standard and IMRT treatment planning systems.

It is yet another object of the invention to provide an improved imaging system that permits an exporting of images to therapeutic treatment planning systems for fusion with either CT or standard simulation images for the localization of internal soft tissue treatment targets.

It is another object of the invention to provide an improved imaging system that provides for rapid patient alignment using ultrasound imaging in accordance with a treatment plan.

It is still another object of the invention to provide an improved treatment system that provides for the accurate localization and targeting of therapy for a soft tissue treatment volume.

It is another object of the invention to provide an improved integrated treatment system that includes a method for confirmation of therapeutic treatment with the treatment plan.

It is yet another object of the invention to provide an improved and integrated treatment system that allows for continuous monitoring during every aspect of a therapeutic treatment procedure.

In accordance with the above objects, the present invention accurately and definitively localizes and fixates the position of a prostate gland (and other portions of the human body) during all phases of the radiation therapy, thus permitting accurate targeting and delivery of escalated dose to the patient without increased morbidity and damage to the surrounding healthy tissues.

Further advantages and features of the present invention will be apparent from the following specifications and claims and drawings illustrating the preferred embodiments of the present invention.

BRIEF DESCRIPTION OF THE DRAWINGS

FIG. 11A is a representation of a ring collar with multiple LED emitters or lights according to an alternate embodiment of the invention; FIG. 11B is a base upon which the ring collar of FIG. 11A is mounted; and FIG. 11C is a side view of the ring collar of FIG. 11A;

FIG. 14A is a representation of a plurality of ultrasound transducers within the head of a transrectal imaging probe; and FIG. 14B is a representation of another configuration of a plurality of ultrasound transducers within the head of a transrectal imaging probe.

DETAILED DESCRIPTION OF THE INVENTION

The present invention comprises a technique and integrated hardware and software system to provide improved planning, registration, targeting, and delivery of conformal, external beam radiation therapy of prostate cancer and other soft-tissue diseases. Real time ultrasound imaging during planning and treatment is used for localization of soft tissue treatment targets and fused with radiographic or CT data for conformal treatment optimization. The fusion technique of the present invention provides accurate localization of the prostate (or other tissue) volume in real time. In particular for treatment of prostate cancer, visualization of the prostate gland is achieved using transrectal ultrasonography and the fusion of that image in the precise location of the prostate within the pelvic region. This makes possible accurate determination of the location of the prostate target by transformation of the ultrasound image data on both the ultrasound and x-ray/CT images. With unambiguous localization of the prostate, the radiation field can be optimized to significantly reduce the volume of irradiated normal tissue, thereby minimizing the exposure of the surrounding healthy tissues and increasing dosage delivered to the prostate treatment target.

Accurate positioning of the ultrasound image relative to the radiation treatment field is achieved using frameless stereotactic image registration. This technique permits very accurate, yet low-cost conformal treatment planning and positioning. Movement of the prostate can be tracked treatment-to-treatment, and the external radiation adjusted in real time, creating a dynamic and adaptive treatment that significantly enhances radiation treatment capabilities while reducing morbidity. This method is applicable to both IMRT as well as conventional planning and treatment delivery. Ultimately this invention provides a new low-cost solution for conformal radiation treatment of the prostate and other internal soft tissues that is consistently more accurate than conventional methods for patient positioning and determination of treatment margins.

Figure 1:
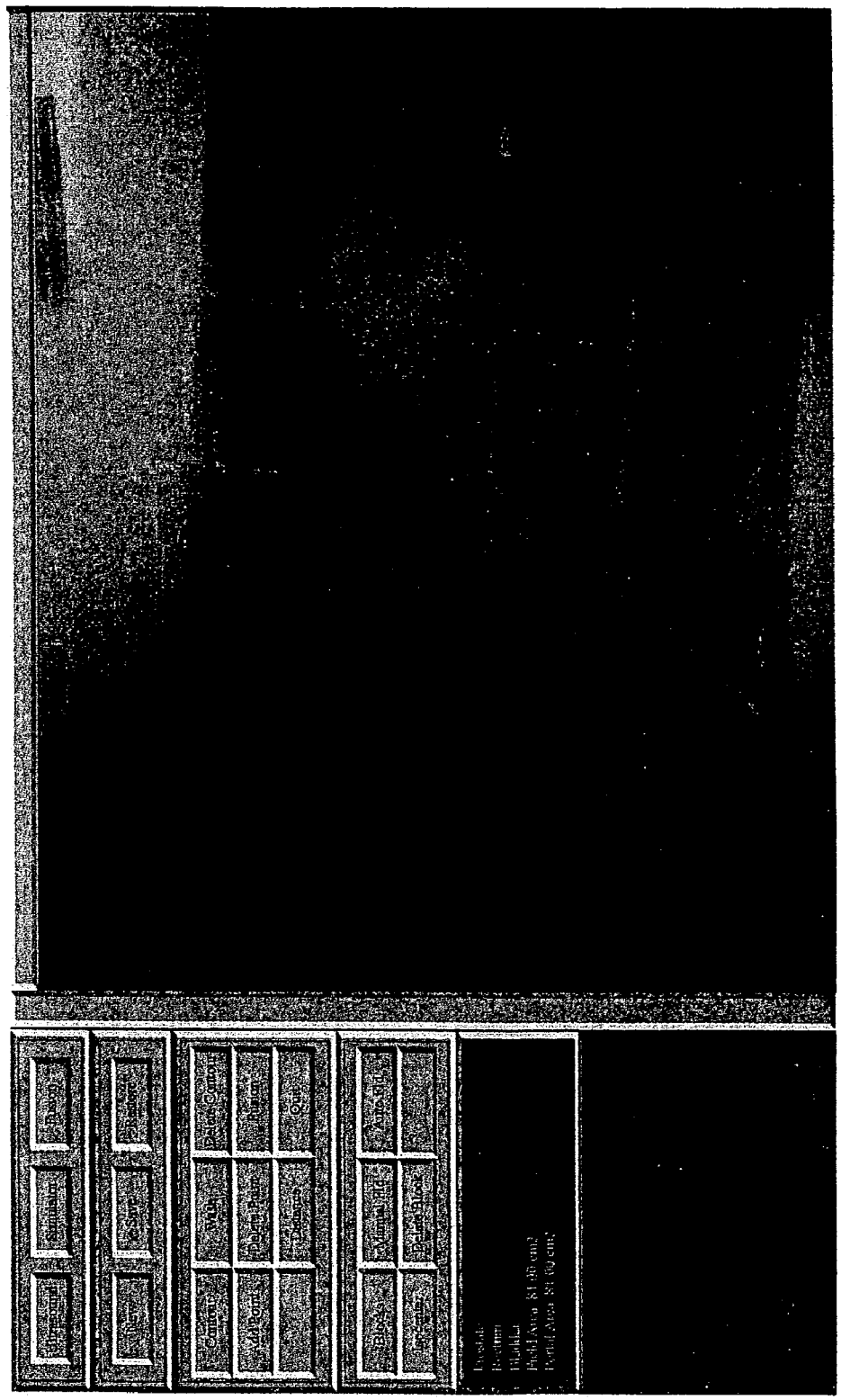
FIG. 1 is a standard treatment planning simulation image for radiation therapy of the prostate, displaying the bones, bladder, and rectum for inferring the position of the prostate, wherein the radiation field zone is superimposed to indicate the region to receive radiation therapy.

The present invention in general comprises the design and use of an integrated system for providing accurate targeting of soft tissues for conformal external beam radiation therapy. Real-time ultrasound imaging during planning and treatment is used for localization of soft tissue targets and fused with radiographic or CT data for conformal treatment optimization. For example, in treatment of prostate cancer, imaging of the prostate gland is achieved using transrectal ultrasonography, and these images are automatically registered to the exact location within the pelvic region. This makes possible accurate targeting of the prostate by transformation and visualization of the ultrasound image data on both the ultrasound images and x-ray/CT images. FIG. 1 is a standard treatment planning simulation image for radiation therapy of the prostate, displaying the bones, bladder, and rectum for inferring the position of the prostate. The radiation field zone is superimposed to indicate the region to receive radiation therapy Some of the key features of the invention relating to the planning stages include the use of an integrated ultrasound system and software, the frameless stereotactic spatial registration of soft tissue images, the generation of anatomy segmentation, the generation of beam's eye views and control of field size, the seamless integration with standard and IMRT treatment planning systems, and the ability to export to treatment planning systems for fusion with either CT or standard simulation images for localizing internal soft tissue treatment targets.

During the treatment stage, the present invention provides for rapid patient alignment using ultrasound imaging with a treatment plan, the accurate localization and targeting of therapy to soft tissue treatment volume, the ability to have confirmation with the treatment plan, and continuous monitoring during each and every treatment.

The preferred form of integrated hardware and software system of the present invention can be separated into five primary components: (1) the ultrasound imaging hardware, (2) the treatment guidance and registration system, (3) the image fusion algorithm and software for treatment planning, (4) the real-time image fusion and localization software for use during the radiation treatment delivery phase, and (5) the computer system used to integrate these components. The following sections provide more details regarding the specific embodiments of this proposed invention.

The ultrasound imaging probe is use to provide sufficient diagnostic imaging of soft tissue while still maintaining a cost-effective system. For the treatment of prostate cancer, the ultrasound imaging hardware system can comprise a standard transrectal ultrasound imaging probe, preferably providing sagittal and transverse views of the prostate. The ultrasound transducer/probe is swept or scanned, either mechanically or electronically, to provide a plurality of two dimensional image slices through the target tissue. The spatial position of each image slice is registered in space, and these two dimensional images are then reconstructed to form a three dimensional image of the target volume used for treatment planning and guidance of the radiation therapy. The ultrasound probe can be held in place by a mechanical stepper or holder device, or the probe can be positioned "freehand" and retained by a support strap to allow the patient to move freely during set-up but prevent the probe from falling out. Although any independent diagnostic system can be used, the ultrasound unit is also preferably integrated with the computer workstation to provide digital control and integration of the ultrasound images with the software applications as well as other imaging sources.

The spatial registration and guidance system of the present invention is used to record the 3-D spatial position of the ultrasound imaging probe at all times, relative to a known reference point. One method to accomplish the registration is through the use of a spatially encoded localizer arm, which tracks the position of the ultrasound probe. The localizer arm holds the ultrasound probe at one end, and is mechanically stabilized or fixed to the treatment table at the other end. The arm can be articulated at several joints, allowing at least three degrees of freedom, and employs encoding devices at these joints to accurately determine the position and orientation of the ultrasound probe relative to the table mount. The localizer arm also allows free movement and positioning of the ultrasound probe, facilitating patient movement during set-up. The localizer arm is used to accurately and reproducibly position the ultrasound probe relative to the center of the radiation field. The positional information of the probe is then conveyed to the image localization software for registration of the images with respect to the treatment iso-center.

Another method to accomplish the spatial registration and guidance of the ultrasound probe is through optical or electromagnetic sensor detection. In this technique, cameras or other concentrated detectors are mounted in the treatment room, and are used to track and register the position of the ultrasound probe or its holder.

As shown in FIGS. 7, 8, 7, 11A and 1C, multiple LED emitters or light sources 40 can be attached to the ultrasound imaging probe or onto a ring collar 42 which is mounted onto the probe 41. The cameras or detectors are then able to determine and record the 3-D position of these light sources 40 in real time, and therefore the position of the ultrasound probe 41, as it is moved freely about near the treatment region of the patient. A simple calibration process can be used to determine the relative spatial position of the ultrasound probe 41 to a known reference frame, as well the registration of the ultrasound images. This calibration information can be stored in a reference file on the computer and used by the software program.

During treatment planning, the image fusion and localization software quantifies the ultrasound imaging plane and combines these ultrasound images with X-ray simulation films to accurately display the location of the prostate relative to the treatment iso-center. This allows the operator to define anatomical contours, radiation beams and shielding blocks so as to conform the treatment optimally to the location and shape of the prostate. This computer software communicates anatomy contours, radiation fields, shielding blocks, ultrasound images, X-ray images, and fused images in electronic form to an external treatment planning system, which the operator can use to perform dose calculations. All structures and images are referenced to the isocenter. One technique for fusing the ultrasound images with the simulation planning image is accomplished in the software program using unambiguous identification of two identical point fiducials on each image. Preferably, the ultrasound device is directly connected to the computer system running this image fusion software, so that the resultant images may be computed and displayed in real time.

For radiation treatment delivery, beam-targeting software is used to display a real-time ultrasound image of the prostate, either in 2-D image slices or a 3-D image volume, which is referenced to the radiation isocenter and superimposed with the beam profiles defined during the treatment planning phase. The image registration and visualization allows the operator to determine whether the patient is optimally positioned to conform with the treatment plan and to make any appropriate adjustments to the patient or the radiation beam to produce optimal targeting. The software program is ideally integrated into the main computer system, but can also be implemented via a network connection.

An integrated computer system, based on a standard personal computer architecture, is preferably used to execute the software programs, as well as to control and coordinate the activities of the other hardware components of the system. In addition to connections with the other hardware components, the computer provides a user interface, high-quality graphic and viewing capabilities, and a standard network interface for communication with other computers, including DICOM servers. The computer also uses appropriate processors, memory storage, and a video/imaging card to provide advanced image processing, computation and real time display capabilities. In addition to the above, the system and software of the present invention can also include additional capabilities relating to the importation and measurement of ultrasound images. For example, the operator can manipulate the system to capture ultrasound images in real time from the ultrasound system via the video capture hardware in the host computer. The system can also maintain at least one "stack" of ultrasound images in a patient file. The system can provide thumbnail views of the ultrasound images, while also allowing the operator to delete images and/or add new images in real time. The system also allows the user to view the X-ray images, one at a time, and will include tools for windowing and leveling, histogram equalization, for example. Furthermore, the user can calibrate the video image by designating specific points within the image (e.g. top center of the probe, and points five cm above and to the right, etc.) and designating which portion of the video image contains valid ultrasound data. The calibration data can then be saved in a configuration file. The user may also adjust brightness, contrast, and/or other basic video parameters, and also specify that multiple frames should be averaged together for noise reduction.

Additionally, the user can calibrate the software for the specific probe. This involves measuring the position and orientation of the image plane relative to the position and orientation of the arm-probe attachment. Alternatively, the user can, in one embodiment of the invention, calibrate the arm and probe together by moving the probe (or a jig attached to the probe) to specific known points referenced to the isocenter. The calibration data is then saved in a configuration file. The software saves captured images in their entirety, as well as the position and orientation of the image plane relative to the isocenter. The software includes a three dimensional view which shows the image slice as it is acquired, within a bounding box with superimposed guide lines through the isocenter; the slice would move in three dimensional space as the ultrasound probe is moved. An ultrasound volume, localized with respect to the isocenter, can be exported in a format suitable for import into the TPS.

Figure 4:
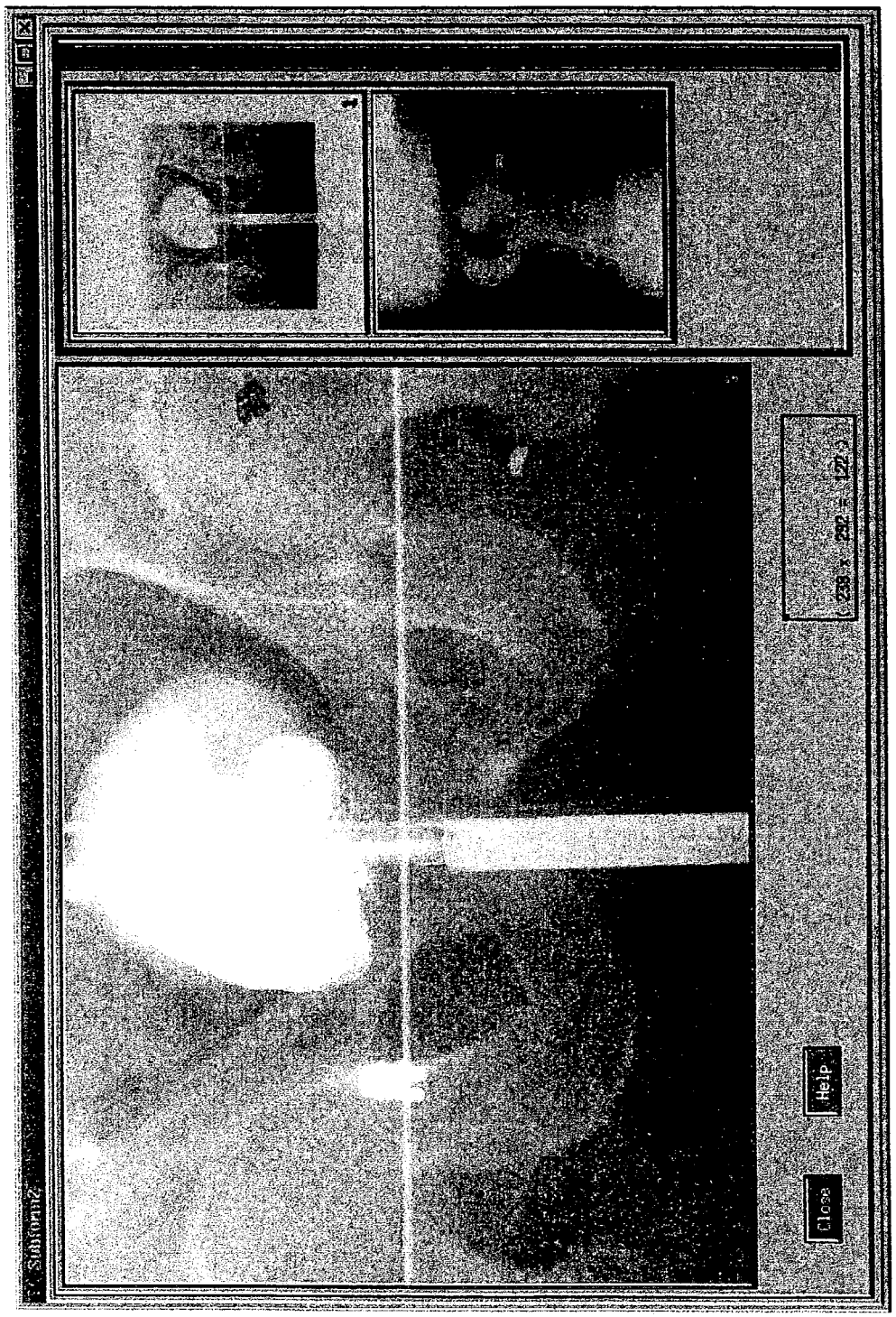
FIG. 4 is an image of a panel displaying the X-ray images read into the software program.

The present invention also provides a number of improved features relating to the importation and management of X-ray images. For example, the present invention allows the operator to import multiple X-ray simulation images. These images are taken from x-ray films which have been scanned into bitmap image files (i.e. jpeg, tiff, etc.). In one embodiment of the invention, the operator can move these files via a network connection to a file server, or via recordable media. For each imported image, the operator must specify a gantry angle to identify the projection of the isocenter in the image the scale of the image (probably by identifying the intersection of fiducial wires in the simulator head, which project into the X-ray image). The operator specifies the geometry of the simulator, including the source-to-isocenter distance and the source-to-film distance. The calibration data is then saved in a configuration file. The system maintains one "set" of X-ray images in a patient file, in addition to provide thumbnail views of the X-ray images, and allows the operator to name, delete and/or add new images to the current set. The system also allows the user to view the x-ray images, one at a time, and will include tools for windowing and leveling, histogram equalization, etc. FIG. 4 Shows a panel for inspecting individual X-ray images that are read into the software program.

Figure 5:
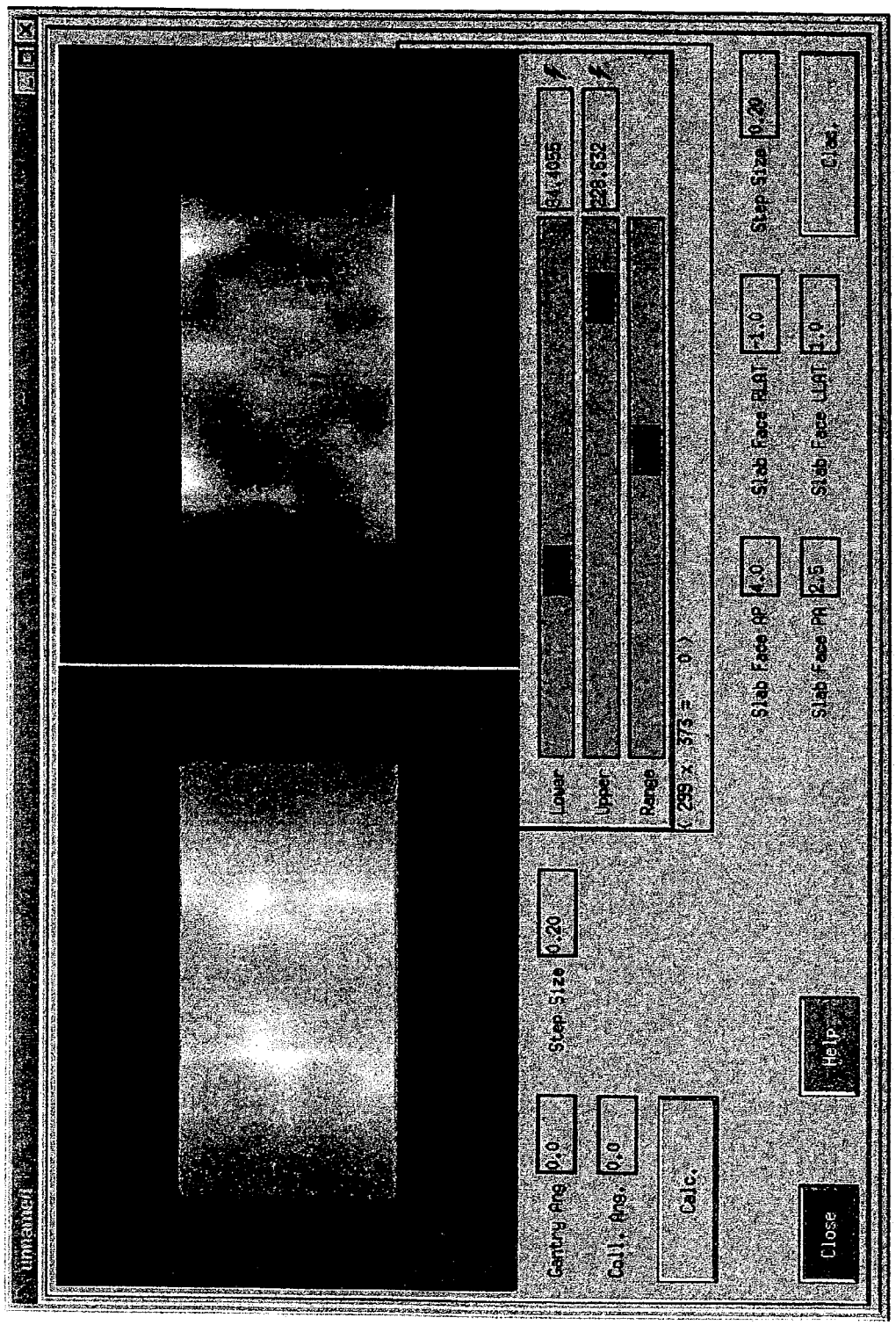
FIG. 5 is an image of a panel for investigating how digitally recomputed ultrasound images (DRU) can be used to obtain information about the prostate, wherein the window on the left-hand side displays an anterior-posterior DRU image calculated using all the data in the ultrasound image set displayed on the panel in the first figure, and the window on the right-hand side displays an anterior-posterior DRU image calculated using only the data points between horizontal planes at 2.5 cm and 4.0 cm away from the axis of the ultrasound probe, in which the prostate can be clearly identified.

Individual X-ray images that are localized with respect to the isocenter may be exported in a format suitable for import into the TPS. The present invention provides an image viewer which allows the user to view X-ray images, superimposing a three-dimensional reconstruction of the ultrasound view volume (DRU) onto the X-ray image. FIG. 5 shows a panel for investigating how digitally recomputed ultrasound images (DRU) can be used to obtain information about the prostate. The window on the left-hand side displays an anterior-posterior DRU image calculated using all the data in the ultrasound image set displayed on the panel in the first figure. The window on the right-hand side displays an anterior-posterior DRU image calculated using only the data points between horizontal planes at 2.5 cm and 4.0 cm away from the axis of the ultrasound probe. In the latter image, the prostate can be clearly identified.

Figure 6:
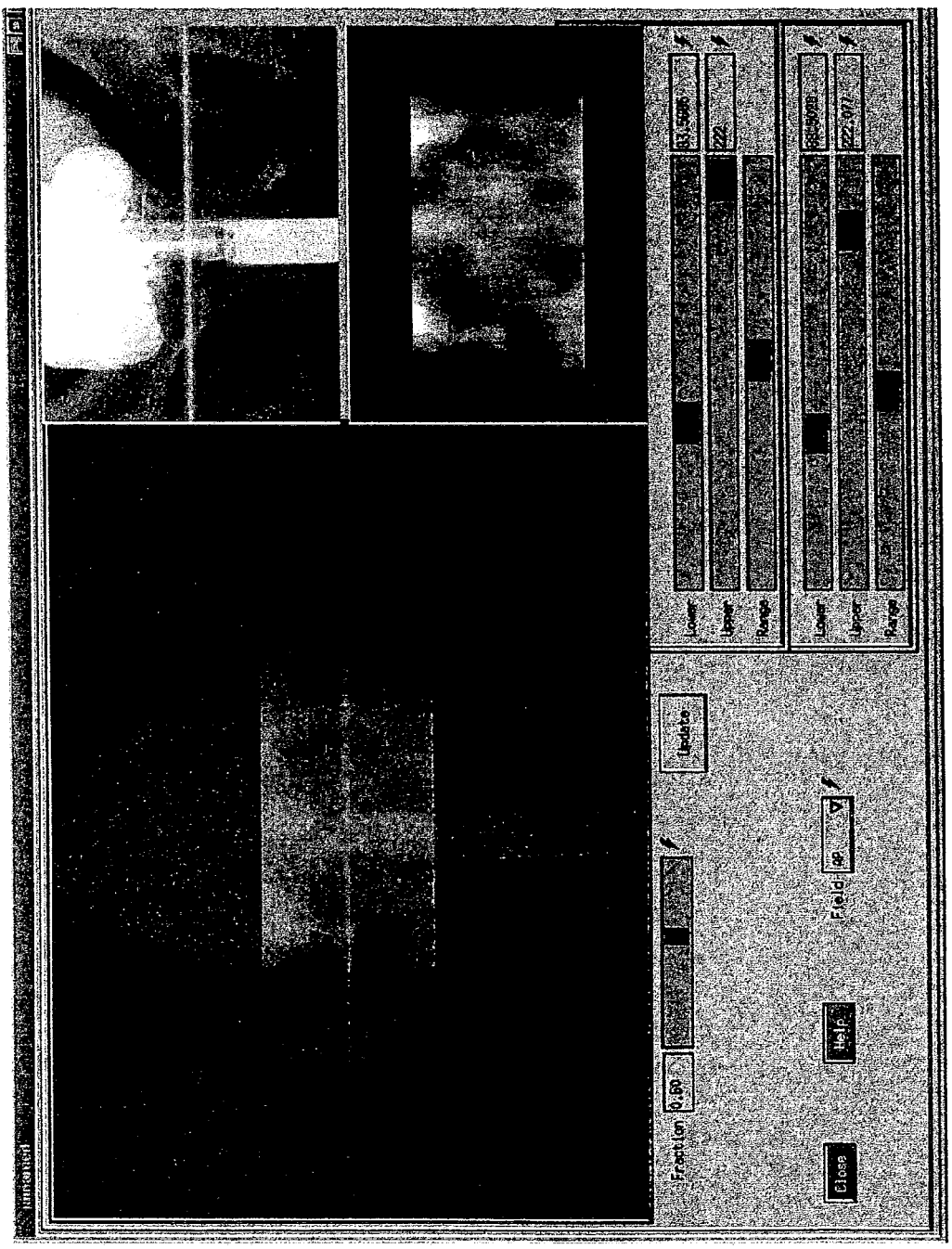
FIG. 6 is an image showing a panel combining an anterior-posterior X-ray image with an anterior-posterior DRU image in the main window, wherein the X-ray image data are displayed using the usual gray-scale method, while the DRU image data have been assigned color cyan (equal green and blue components), and wherein the upper and lower windows on the right-hand side display the original X-ray image and DRU image, respectively.
Figure 7:
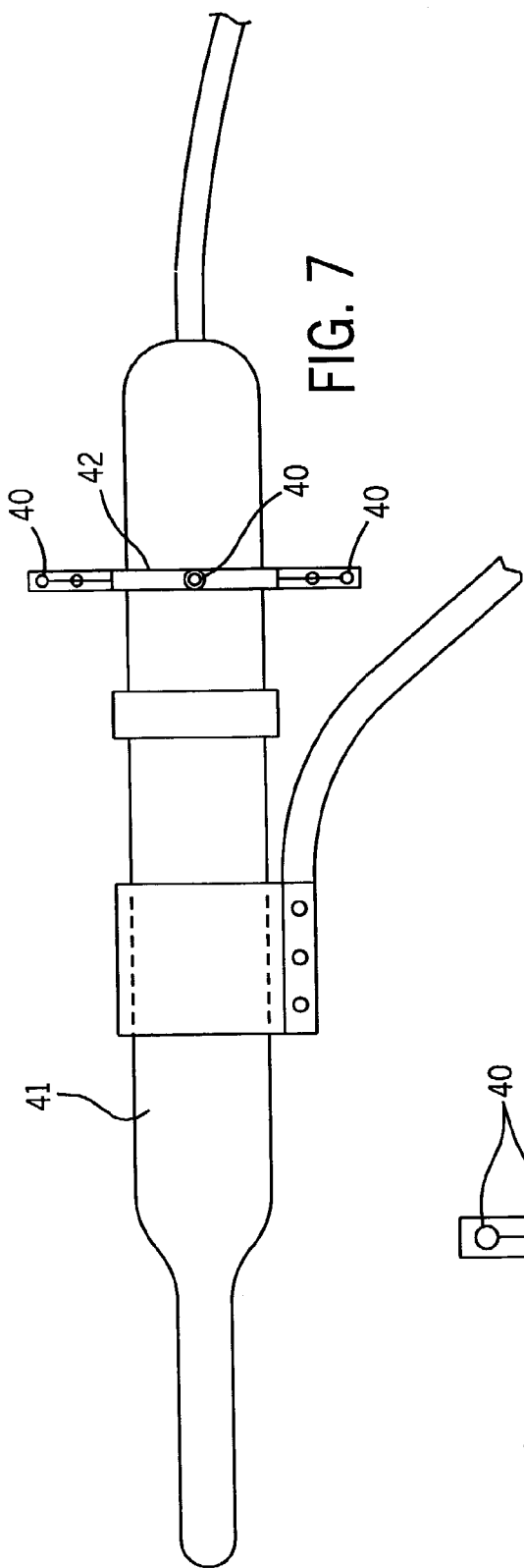
FIG. 7 is a representation of a transrectal ultrasound probe mounted with a ring collar containing LED emitters or lights on the surface to allow tracking the probe position with an optical registration system.
Figure 10:
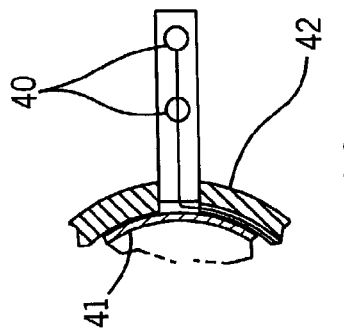
FIG. 10 is yet another representation of an alternate configuration for mounting the LEDs or light sources onto the surface of a ring collar.
Figure 9:
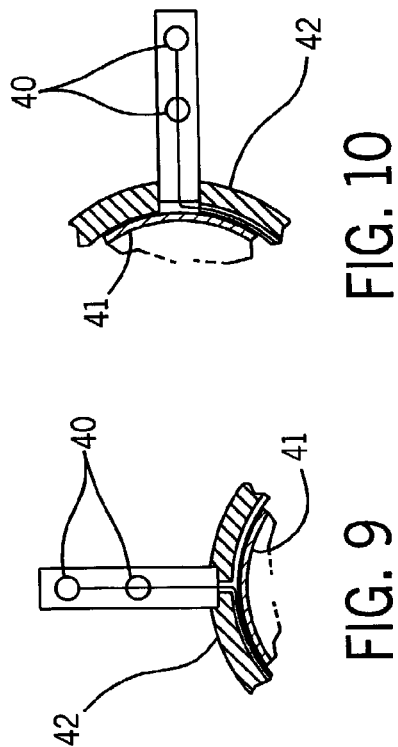
FIG. 9 is a representation of an alternate configuration for mounting the LEDs or light sources onto the surface of a ring collar.
Figure 8:
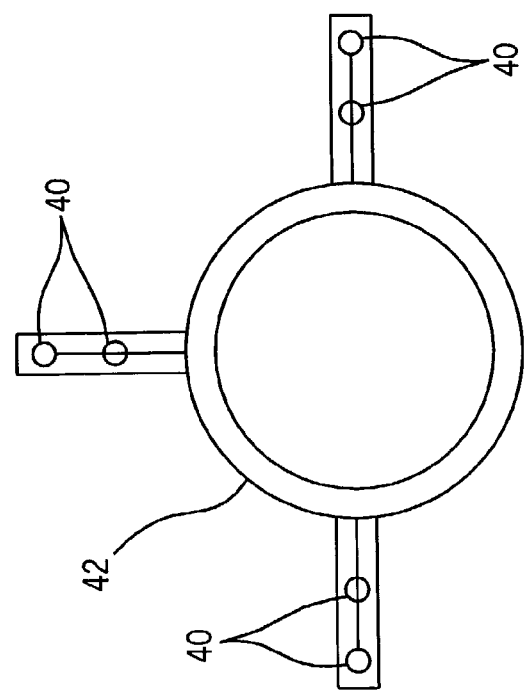
FIG. 8 is an end view of the ring collar shown in FIG. 7, containing multiple LED emitters or lights for tracking with the optical registration system, wherein the ring collar mounts onto the ultrasound transrectal probe.

The DRU is divergent, meaning that the individual rays projected through the ultrasound view volume diverge along a line from the radiation source, which is assumed to be a point source. The operator can "blend" the DRU and X-ray image to varying degrees, allowing the user to clearly view the location of the prostate within the X-ray image. Fused images may be exported in a format suitable for import into the treatment planning software. FIG. 6 shows a panel combining an anterior-posterior x-ray image with an anterior-posterior DRU image in the main window, wherein the x-ray image data are displayed using the usual gray-scale method, while the DRU image data have been assigned color cyan (equal green and blue components). The upper and lower windows on the right-hand side display the original X-ray image and DRU image, respectively For contouring, the present invention provides the user with the ability to draw anatomical contours, using the ultrasound data as a guide. The user also has the ability to contour in either 2-D or 3-D modes. Contours can be accepted for multiple anatomies and identified by name. The user can also designate new structures to be contoured and assign names to the new structures. Contours can also be exported in a format suitable for import into the TPS.

Regarding the radiation fields involved with the present invention, the present invention permits the operator to resize proposed treatment fields, using the fused image (X-ray film with DRU and/or contours superimposed) as a guide. One field is saved for each X-ray film. The operator can specify the size constraints on the field dimensions and whether or not the field must remain symmetric about the isocenter ("symmetric jaws" constraint) based on the capabilities of the linear accelerator. The calibration data is then saved in a configuration file. The beam profiles may be exported in a format suitable for import into the TPS.

The present invention also allows the operator to draw "blocks" on the proposed treatment fields. The blocks are thick Cerrobend (Pb—Cd) alloy blocks which are used to collimate or shield the corners of the treatment field from radiation and to conform the radiation to the beam's-eye cross-section of the prostate. The operator can specify a margin, which is the extent to which the block extends beyond the edge of the field. The margin is required to allow the blocks, which may be exported in a format suitable for import into the TPS, to be physically attached to the carrier which is placed into the head of the linear accelerator. The calibration data will be saved in a configuration file. The operator can print the blocks, scaled by an operator-specified scale factor, as "blueprints" to be used by personnel who fabricate the blocks for a specific patient. The scale factor is saved in a configuration file.

The system and software allows the operator to view the ultrasound image data in real time, as it is acquired. The location of the ultrasound image is known based on the table position and the localizer arm.

The operator can superimpose the original prostate contours, and/or the geometry of any one of the treatment beams (field, blocks, etc.) on the image slice view, allowing the operator to determine whether or not the prostate is positioned as planned. This feature may be used at treatment time to assist in aligning the patient with the isocenter and making sure that the prostate remains in its expected location for the duration of the treatment. Involuntary patient movement, gas passing through the bowel, etc. can also cause the prostate to move during treatment.

The system of the present invention also has the ability to store all data, images, settings, etc. associated with a particular patient in a "patient file," including administrative information (patient name, physician's name, institution, etc.). A configuration file contains the calibration settings for the application. The operator can also name, save, and load configurations.

Figure 2:
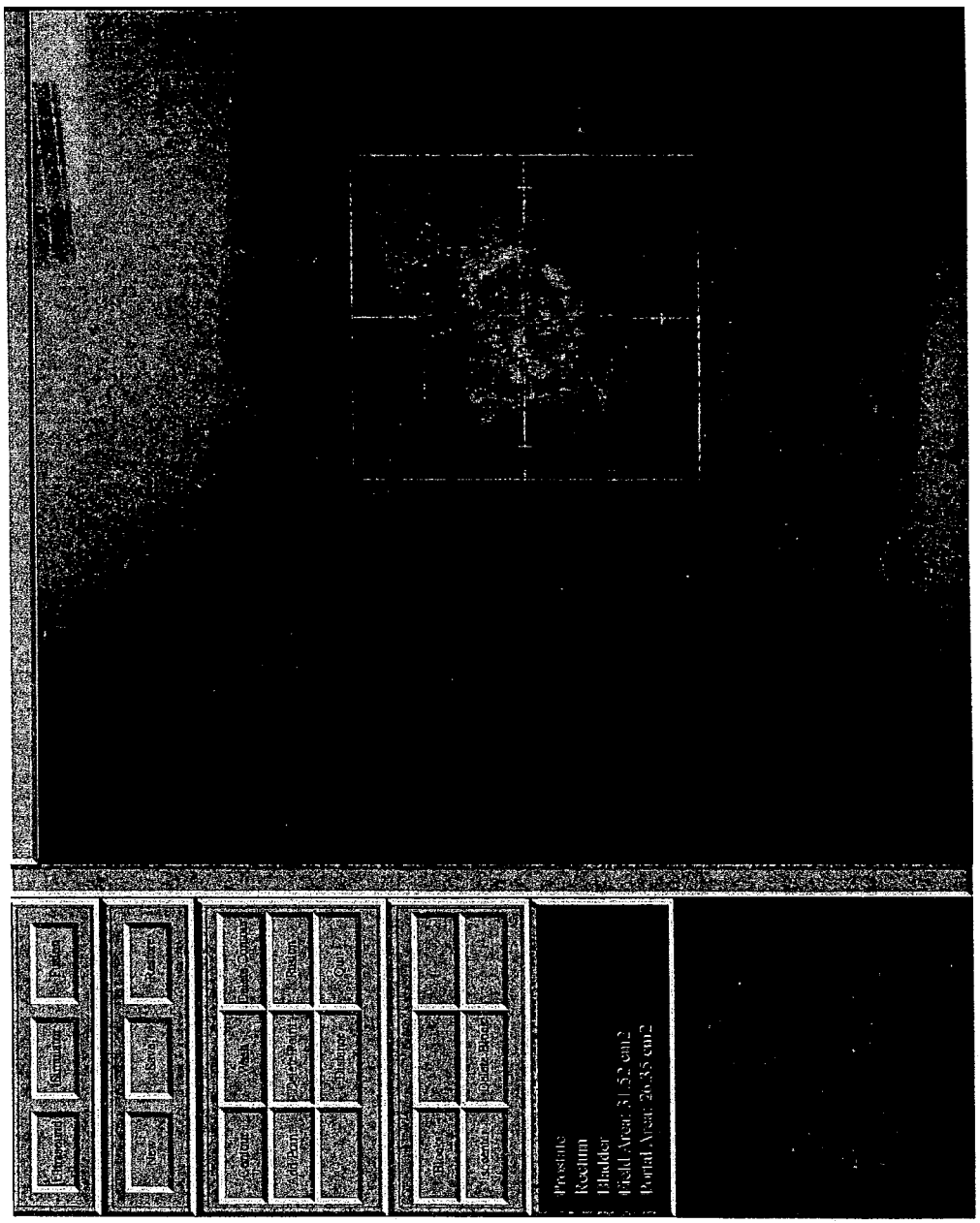
FIG. 2 is an image showing the fusion of the ultrasound image to the X-ray simulator image, together with the new superimposed radiation field zone, wherein the interior outline displays the size of the treatment field necessary to completely treat the prostate as determined by the ultrasound guided technique and the exterior outline displays the size of the treatment field as determined by the conventional technique, and wherein the prostate and other structures are visible in the fused image which were not visible in the X-ray simulation alone.

In addition to the actual system for improved targeting of external beam radiation therapy, new steps are also involved in the treatment model of the present invention. In preparation for a simulation, a technician mounts the probe and registration system to the simulation table. Using a combination of probe movement and the system's user interface, the technician calibrates the registration system relative to the simulated isocenter. The ultrasound probe is then inserted during the simulation process. Using the system's user interface, the user acquires a three-dimensional ultrasound view volume including the prostate. The user may need to manipulate the ultrasound probe in order to ensure that the prostate is enclosed within the extent of the probe's three-dimensional view. The probe remains in place while the simulation data (CT or X-ray images) are captured in the normal manner. The image fusion software is used to combine the image data acquired from the simulator with the isocenter-referenced ultrasound view volume provided by the registration system. The result is a fused set of images or a fused view volume in which the prostate is clearly visible. FIG. 2 shows the fusion of the ultrasound to the X-ray simulator image, together with the new superimposed radiation field zone. The interior outline displays the size of the treatment field necessary to completely treat the prostate as determined by the ultrasound guided technique and the exterior outline displays the size of the treatment field as determined by the conventional technique. The prostate and other structures are visible in the fused image which were not visible in the X-ray simulation alone. It is important to note that the high-dose radiation field is confined to the prostate with minimal involvement of nearby critical structures such as the bladder and rectum.

Figure 3:
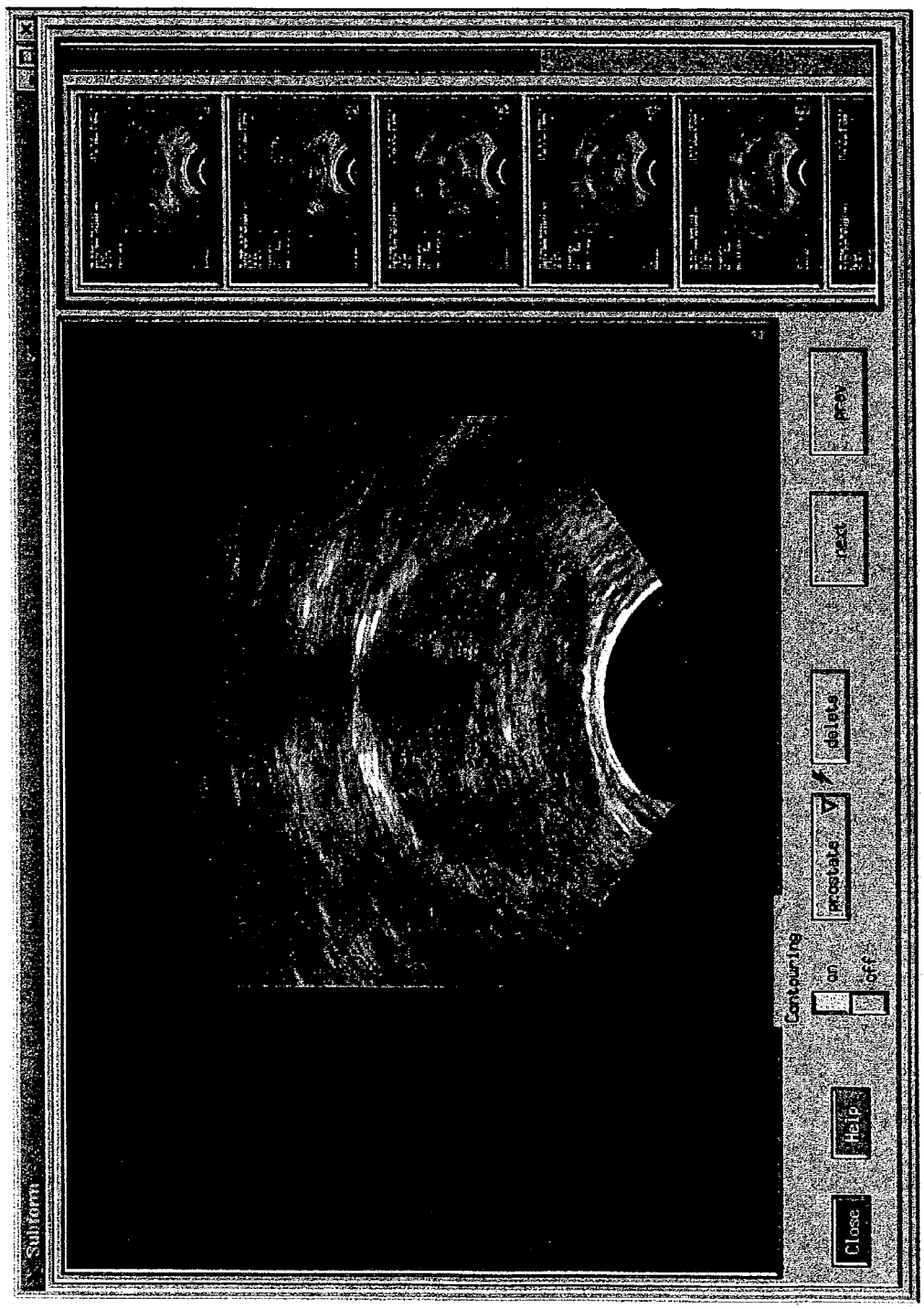
FIG. 3 is an image of a panel displaying on the right hand side a set of ultrasound images that have been read into the software planning program, while also displaying in the main window a selected image with markings removed.

Treatment planning is conducted in a manner similar to the conventional model described herein using an existing Treatment Planning System. The fused image data used during treatment planning allows the radiation oncologist to easily identify the exact location and extent of the prostate. A technician mounts the probe and registration localizer arm to the treatment table. Using a combination of probe movement and the system's user interface, the technician then calibrates the probe localizer relative to the LINAC isocenter. The ultrasound probe is then inserted. At that point, the system can provide real-time three-dimensional ultrasound data, spatially referenced to the treatment isocenter. FIG. 3 shows an image of a panel displaying on the right hand side a set of ultrasound images that have been read into the software planning program. A selected image with markings removed is shown in the primary window.

The beam-targeting and guidance software, using real-time images from the image-registration system and information from the treatment plan, allows a technician to view the ultrasound image of the prostate with the beam geometry and original prostate contours superimposed. The technician adjusts the position of the patient and/or the treatment table to align the prostate as closely as possible with the original prostate contours and verify that the beam is conformal with the prostate. During treatment, the user monitors the real-time display of the prostate and treatment geometry, ensuring that the radiation beams remain conformal to the prostate throughout the treatment.

The following describes how the preferred system of the present invention addresses the problems and limitations previously identified in the conventional treatment model. At simulation time, the image-registration system is mounted to the simulation table and calibrated by an operator with respect to the simulated isocenter. The transrectal probe is then inserted into the patient during simulation. After the resulting X-ray images or CT view volume have been prepared for import into the treatment planning system, the image fusion software is used to fuse the ultrasound data (on which the prostate is clearly visible) into the simulation data. The enhanced data is then imported into the TPS and allows the oncologist to clearly identify the location and extent of the prostate with respect to the treatment isocenter, allowing highly conformal beams to be defined.

At treatment time, the image-registration system is mounted to the treatment table and calibrated by an operator with respect to the treatment isocenter. The transrectal probe is then inserted into the patient during treatment. The beam geometry information provided by the TPS is imported into the beam-targeting software, which provides the operator with an image of the prostate referenced to the treatment isocenter. By comparing the location and extent of the prostate as drawn at treatment time with the actual location and extent of the prostate as indicated by the ultrasound image, the operator can adjust the position of the patient. The high degree of beam/prostate conformance assumed during treatment planning can thus be maintained throughout the duration of the treatment. In addition, the presence of the transrectal probe helps to ensure consistency in prostate position for each treatment.

The image-registration system provides a real-time image of the prostate during treatment. The beam-targeting software is used to view this real-time image. Monitoring of position during treatment will permit the operator to stop treatment if the patient position changes.

The presence of the transrectal probe during treatment displaces the posterior side of the rectum away from the prostate. The use of the transrectal probe during simulation and treatment helps maintain a consistent spatial relationship between the rectum, bladder neck, and prostate throughout the simulation and treatment process. This allows excessive exposure of the rectal wall and bladder neck to be avoid, and the conformal treatment plan margins to be ensured.

The probe or imaging device of the present invention is maneuverable in space but does not have to be tied to an encoded arm or a similar structure. The probe of the present invention can be moved in several directions. In one preferred embodiment of the invention, the probe is an ultrasound imaging probe that creates images. Unlike conventional imaging and treatment systems, the created images do not have to be combined from a stack of parallel images or from a sweep of multiple images through an angular sweep. It can be in any arbitrary position in space. And, the user knows where it is in space at all times by the use of points on this imaging device. The device collects the data, and a combination of optical and electromagnetic devices are positioned around the room that work together and spatially localize where this the imaging device is grounded via points on the imaging device or probe and. The image's location in space is already known and is produced by the imaging probe relative go the points so that is already a given because that is fixed since they are all on the same device. This provides the special relationship to the user; and because the user knows that the points are relative to the device and from the accommodation of the optical electromagnetic system (which can also be a simple optical system alone or an electromagnetic system alone depending on the embodiment), the position of the device is determined.

Figure 12:
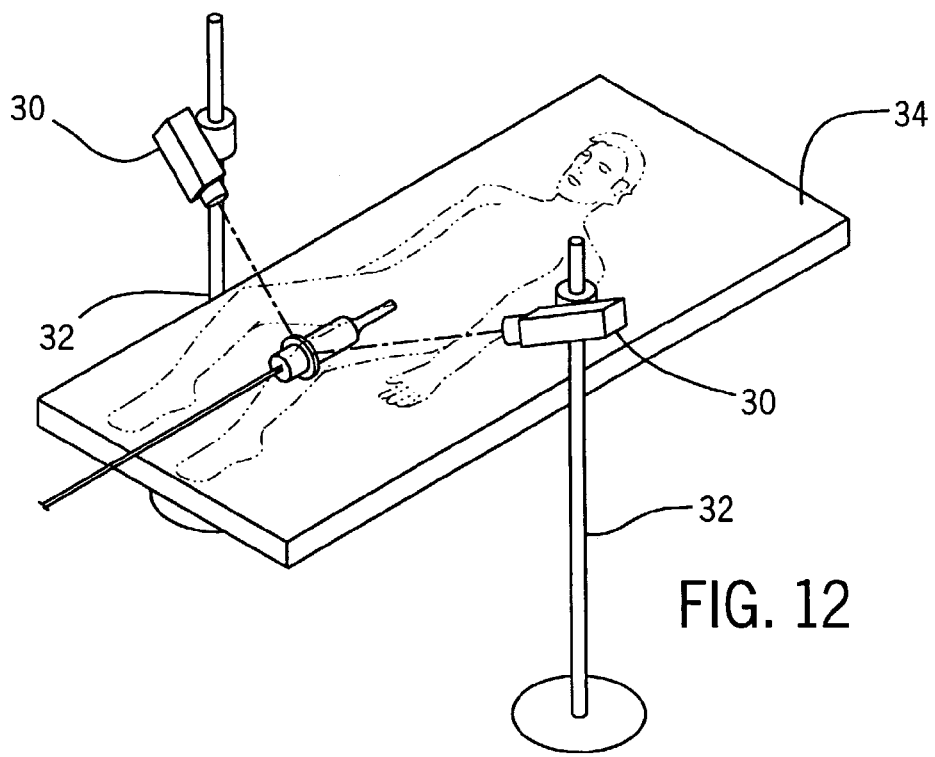
FIG. 12 is a representation of a room setup of one example of the system of the present invention for the treatment of prostate cancer, including an optical registration system with two cameras mounted adjacent to a patient table for tracking the three-dimensional spatial position of the LEDs mounted on the transrectal ultrasound imaging probe.
Figure 13:
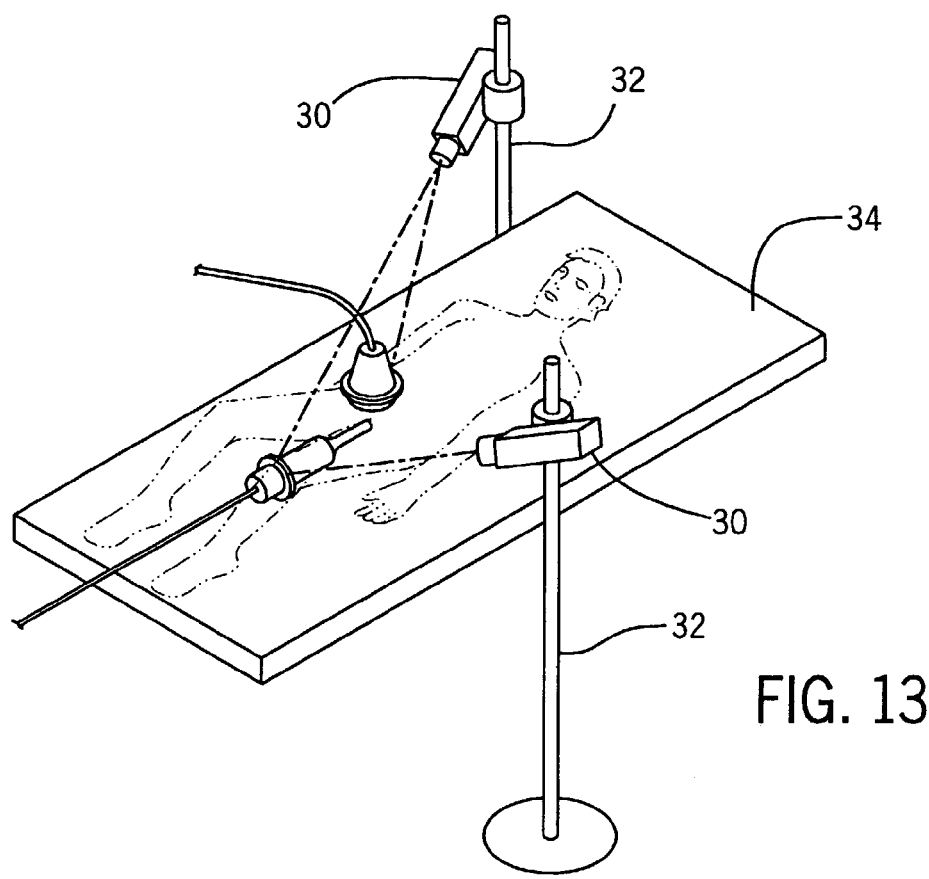
FIG. 13 is another representation of a room setup of another example of the system of the present invention for the treatment of prostate cancer, including an optical registration system with two cameras mounted adjacent to a patient table for tracking the three-dimensional spatial position of the LEDs mounted on the transrectal ultrasound imaging probe.

FIGS. 12 and 13 show a generic setup of the system according to one embodiment of the present invention. A pair of cameras 30 are mounted on stands 32 on opposite sides of a patient table 34.

The information provided above is taken by the related software and is converted into a three dimensional image volume. Not only does this system render the volume, but it also permits the user to manipulate the volume. For example, a user could literally use a computer mouse to click on points on the surface of that volume. The system will then generate a surface rendering that matches that exact volume shape of the actual intrinsic image data set that is underneath it and create volume information or other information. Individual locations on the surface can be mapped, and a complete volume contour can be shown of the surface using as few as 8 or 9 or 10 points or as many as 20 or 30 or 40 points. For example, this system is very useful in treatment of prostate disease because the user can identify an exact position in space in the body without having to have all of several fixtures, encoded arms and a stepping device that have positional encoding on the stepping.

While the preferred embodiments of the invention have been described, it will be understood by those skilled in the art to which the invention pertains that numerous modifications and changes may be made without departing from the true spirit and scope of the invention. The embodiments described herein are accordingly intended to define the scope of the invention precisely in the claims appended to and forming a part of this application.

The invention claimed is:

1. A system for creating fused images for use in targeting external beam radiation therapy comprising:
   an ultrasound probe configured to produce ultrasound images of a proposed treatment region;
   a probe locator system configured to locate the position of the ultrasound probe, wherein the probe locator system comprises a frameless spatial registration system, and wherein the frameless spatial registration system comprises an emitter and sensor system;
   a computer system connected to the probe locator system and ultrasound probe, said computer system having a software program configured to spatially register the ultrasound images according to the located probe position and fuse the spatially registered ultrasound images with either radiographic images of the proposed treatment region or a treatment planning image;
   a ring collar within which the ultrasound probe is disposed, and wherein the emitter and sensor system comprises a plurality of LEDs attached to the ring collar and at least one camera for detecting the three-dimensional position of the LEDs relative to the treatment region;
   wherein said computer system further comprises treatment planning software for defining a treatment beam based at least in part upon a position of a desired target volume in the treatment region, the position being determinable within a fused image generated during a treatment planning session;
   wherein the fused image generated during the treatment planning session is a volumetric representation of the treatment region; and
   wherein the treatment planning software is further configured to (1) display the volumetric image and (2) contour the target volume in response to user input.

2. The system of claim 1 further comprising a treatment device in communication with the computer system for delivering external beam radiation therapy to the target volume at least partially in accordance with the defined treatment beam.

3. The system of claim 2, wherein the target volume is a patient's prostate.

4. The system of claim 2, wherein the treatment device is a linear accelerator (LINAC).

5. The system of claim 2, wherein the computer system further comprises software for displaying a superimposed image of the treatment beam defined by the treatment planning software over a fused image of the treatment region generated during a treatment delivery session, to thereby allow a determination of whether any movement of the target volume from the time of the treatment planning session necessitates a modification of either the patient's position or the treatment beam.

6. The system of claim 5 wherein the computer system further comprises software for modifying the treatment beam at least partially in accordance with the position of target volume as determined from the fused image generated during the treatment delivery session.

7. The system of claim 5, wherein the fused image generated during the treatment delivery session is a volumetric representation of the treatment region.

8. The system of claim 7, wherein the computer system further comprises software for generating and displaying the fused image generated during the treatment delivery session in real-time.

9. The system of claim 1, wherein the treatment planning software is further configured to define the treatment beam such that it is targeted on the contoured target volume.

10. The system of claim 1, wherein the ultrasound probe is a freehand ultrasound probe.

11. The system of claim 10, wherein the freehand ultrasound probe is a transrectal freehand ultrasound probe.

12. The system of claim 1, wherein the computer system is configured to import a radiation therapy treatment plan from another computer, wherein the plan comprises a plurality of spatially registered images of the treatment region that were generated during a treatment planning session.

13. The system of claim 12 wherein the plan further comprises a treatment beam definition for targeting a treatment beam on a target volume shown in the plan's spatially registered images.

14. A method of creating a spatially registered fused image of a target volume within a treatment region inside a patient for planning an external beam radiation therapy treatment session, the method comprising:
   generating a plurality of ultrasound images of the target volume using a transrectal ultrasound probe that has been inserted into the patient's rectum;
   spatially registering the ultrasound images relative to a known coordinate system;
   generating a three-dimensional representation of the target volume from the spatially registered ultrasound images;
   generating at least one simulation image of the treatment region while the transrectal ultrasound probe is still inserted in the patient's rectum, the simulation image having a known position and orientation relative to the coordinate system;
   fusing the three-dimensional target volume representation with the at least one simulation image such that the three-dimensional target volume representation and the at least one simulation image are both spatially registered relative to a common point of reference; and
   graphically displaying the fused image of the three-dimensional target volume representation and the at least one simulation image.

15. The method of claim 14, wherein the common point of reference comprises a treatment isocenter of an external radiation treatment beam, the method further comprising:
   defining, via user input, the treatment beam targeted to the treatment isocenter; and
   graphically displaying the defined treatment beam such that it is superimposed over the fused image.

16. The method of claim 15 further comprising three-dimensionally contouring the target volume within the fused images in response to user input through the graphically displayed fused image to create a three-dimensional contour of the target volume.

17. The method of claim 16 further comprising:
   generating and graphically displaying a real-time three dimensional representation of the target volume from the images acquired by the inserted transrectal ultrasound probe;
   spatially registering the real-time three dimensional target volume representation relative to the treatment isocenter; and superimposing the three-dimensional target volume contour over the real-time three dimensional target volume representation such that both are spatially registered relative to the treatment isocenter.

18. The method of claim 17, wherein the generating and graphically display step comprises:
fusing the at least one simulation image with the generated real-time three dimensional target volume representation, thereby creating a fusion of the generated real-time three dimensional target volume representation and the at least one simulation image; and
graphically displaying the fusion of the generated real-time three dimensional target volume representation and the at least one simulation image; and
wherein the superimposing step comprises superimposing the three-dimensional target volume contour over the fusion of the real-time three dimensional target volume representation and the at least one simulation image such that both are spatially registered relative to the treatment isocenter.

19. The method of claim 18 wherein the at least one simulation image comprises at least one selected from the group consisting of an X-ray image and a computed tomography (CT) image.

20. The method of claim 17 further comprising:
adjusting a position of the patient if the graphically displaying step and the superimposing step reveals a misalignment between the target volume in the real-time three dimensional target volume representation and the target volume in the three-dimensional target volume contour.

21. The method of claim 17 further comprising:
superimposing the defined treatment beam over the three-dimensional target volume contour and the real-time three dimensional target volume representation such that the defined treatment beam, the three-dimensional target volume contour, and the real-time three dimensional target volume representation are all spatially registered relative to the treatment isocenter.

22. The method of claim 17 further comprising:
delivering a treatment beam in accordance with the defined treatment beam to the target volume while the transrectal ultrasound probe is still inserted in the patient's rectum.

23. The method of claim 22 wherein the transrectal ultrasound probe comprises a freehand transrectal ultrasound probe.

24. The method of claim 22 wherein the transrectal ultrasound probe comprises a transrectal ultrasound probe that is attached to a spatially-encoded localizer arm.

25. The method of claim 15, wherein the beam defining step comprises defining a treatment beam isocenter that is targeted on the target volume.

26. The method of claim 25, wherein the beam defining step further comprises defining treatment beam geometry data.

27. The method of claim 26, wherein the beam defining step further comprises defining a beam energy amount.

28. The method of claim 26, wherein the beam defining step further comprises defining a shield block for the treatment beam.

29. The method of claim 28 wherein the shield block defining step comprises defining a margin for the shield block.

30. The method of claim 26 further comprising storing the treatment beam definitions for subsequent retrieval during a treatment delivery session.

31. The method of claim 26 wherein the beam defining step further comprises defining whether the treatment beam is to be symmetric about the treatment isocenter.

32. The method of claim 15, wherein the target volume is a patient's prostate.

33. The method of claim 14 further comprising storing the fused images for subsequent retrieval during a treatment delivery session.

34. The method of claim 14, wherein the ultrasound image generating step comprises generating the plurality of ultrasound images of the target volume using the inserted transrectal ultrasound probe at any arbitrary position in space, and wherein the three-dimensional target volume representation generating step comprises generating the three-dimensional target volume representation from the spatially registered ultrasound images acquired by the inserted transrectal ultrasound probe at any arbitrary position in space.

35. The method of claim 34, wherein the three-dimensional target volume representation generating step comprises generating the three-dimensional target volume representation not from ultrasound images within a stack of parallel images of the target volume nor from a series ultrasound images of the target volume that were acquired by the inserted transrectal ultrasound probe via an angular sweep.

36. An external beam radiation therapy system for planning and delivering external beam radiation treatment for a target volume that resides within a treatment region inside a patient, the patient residing in a treatment coordinate system, the system comprising:
an imaging device for generating a plurality of images of the target volume;
a localization system associated with the imaging device that locates the imaging device within the coordinate system; and
a computer that executes software programmed to (1) spatially register the images relative to a point of reference within the coordinate system on the basis of data provided by the localization system, (2) generate a three-dimensional representation of the target volume from the spatially registered images, (3) retrieve at least one stored treatment planning simulation image of the treatment region, wherein the treatment planning simulation image is also spatially registered relative to a point of reference within the coordinate system, (4) fuse the three-dimensional target volume representation with the treatment planning simulation image, and (5) graphically display the fused image such that the three-dimensional target volume representation is superimposed over the treatment region depicted in the treatment planning simulation image in a manner such that both the target volume representation and the treatment region are spatially registered relative to a common reference point within the coordinate system.

37. The system of claim 36 wherein the common point of reference within the coordinate system comprises a treatment isocenter of an external radiation beam.

38. The system of claim 37, wherein the imaging device comprises a transrectal ultrasound probe.

39. The system of claim 38, wherein the target volume comprises a patient's prostate.

40. The system of claim 39 wherein the computer is further programmed to three-dimensionally contour the patient's prostate volume from the graphically displayed fused image in response to user input.

41. The system of claim 40 wherein the computer is further programmed to (1) define a planned beam profile for the external radiation beam in response to user input through the graphically displayed fused image, and (2) graphically depict the defined planned beam profile superimposed over the fused image such that the defined planned beam profile is also spatially registered relative to the treatment isocenter.

42. The system of claim 41 further comprising an external beam radiation therapy treatment device in communication with the computer, the treatment device having a coordinate system within which it can deliver a targeted radiation beam centered about the treatment isocenter in accordance with the defined planned beam profile.

43. The system of claim 42, wherein the computer is further programmed to graphically display a real-time three-dimensional digitally reconstructed ultrasound volume of the prostate, and wherein the three-dimensional contour and the defined planned beam profile are superimposed over the real-time three-dimensional digitally reconstructed ultrasound prostate volume such that the real-time three-dimensional digitally reconstructed ultrasound prostate volume, the three-dimensional contour, and the defined planned beam profile are all spatially registered relative to the treatment isocenter.

44. The system of claim 43, wherein the computer is further programmed to graphically display the real-time three-dimensional digitally reconstructed ultrasound prostate volume by fusing it with the at least one treatment planning simulation image such that a fusion of the real-time three-dimensional digitally reconstructed ultrasound prostate volume and the at least one treatment planning simulation image is graphically displayed.

45. The system of claim 41 wherein the computer is further programmed to accept user input for the planned beam profile corresponding to a size constraint for the beam.

46. The system of claim 41 wherein the computer is further programmed to accept user input for the planned beam profile corresponding to whether the beam is to be symmetric about the treatment isocenter.

47. The system of claim 41 wherein the computer is further programmed to accept user input for the planned beam profile corresponding to a block on a treatment field provided by the planned beam profile.

48. The system of claim 47 wherein the computer is further programmed to accept user input corresponding to a margin for the block.

49. The system of claim 41 wherein the computer is further programmed to accept user inputs for the planned beam profile corresponding to a size constraint for the beam, corresponding to whether the beam is to be symmetric about the treatment isocenter, and corresponding to a block on a treatment field provided by the planned beam profile.

50. The system of claim 41 wherein the computer is further programmed to graphically display the defined planned beam profile such that it is also superimposed over the three-dimensional contour and the fused image.

51. The system of claim 38, wherein the localization system comprises a frameless localization system.

52. The system of claim 51, wherein the frameless localization system comprises an emitter and sensor localization system.

53. The system of claim 51, wherein the frameless localization system comprises an optical localization system.

54. The system of claim 38, wherein the transrectal ultrasound probe comprises a freehand transrectal ultrasound probe.

55. The system of claim 36, wherein the at least one treatment planning simulation image comprises an X-ray image.

56. The system of claim 36, wherein the at least one treatment planning simulation image comprises a computed tomography (CT) image.

57. The system of claim 36, wherein the computer is further programmed to generate the three-dimensional representation of the target volume from the spatially registered images using spatially registered images of the target volume that were acquired by the imaging device at any arbitrary position in space within the treatment coordinate system.

58. The system of claim 57, wherein the computer is further programmed not to generate the three-dimensional representation of the target volume from the spatially registered images using a stack of parallel images of the target volume that were acquired by the imaging device.

59. The system of claim 57, wherein the computer is further programmed not to generate the three-dimensional representation of the target volume from the spatially registered images using a series images of the target volume that were acquired by the imaging device via an angular sweep.

* * * * *